(12) United States Patent
Ueno et al.

(10) Patent No.: US 9,334,492 B2
(45) Date of Patent: May 10, 2016

(54) PROTEIN-IMMOBILIZING SOLID PHASE, POLYNUCLEOTIDE-IMMOBILIZING SOLID PHASE, AND NUCLEIC ACID RECOVERY METHOD

(71) Applicants: The University of Tokyo, Tokyo (JP); Nikon Corporation, Tokyo (JP)

(72) Inventors: Shingo Ueno, Tokyo (JP); Naoto Nemoto, Tokyo (JP); Takanori Ichiki, Tokyo (JP); Hirofumi Shiono, Fujisawa (JP); Hisao Osawa, Kashiwa (JP)

(73) Assignees: The University of Tokyo, Tokyo (JP); NIKON CORPORATION, Tokyo (JP)

( * ) Notice: Subject to any disclaimer, the term of this patent is extended or adjusted under 35 U.S.C. 154(b) by 15 days.

(21) Appl. No.: 14/266,185

(22) Filed: Apr. 30, 2014

(65) Prior Publication Data

US 2014/0296111 A1 Oct. 2, 2014

Related U.S. Application Data

(63) Continuation of application No. PCT/JP2012/078321, filed on Nov. 1, 2012.

(30) Foreign Application Priority Data

Nov. 4, 2011 (JP) .................. 2011-242789

(51) Int. Cl.
| | |
|---|---|
| C40B 40/08 | (2006.01) |
| C40B 50/18 | (2006.01) |
| C12Q 1/68 | (2006.01) |
| C12P 19/34 | (2006.01) |
| C12N 11/00 | (2006.01) |
| C12N 11/16 | (2006.01) |
| C07H 19/00 | (2006.01) |
| G01N 31/22 | (2006.01) |
| G01N 33/52 | (2006.01) |
| C12N 15/10 | (2006.01) |
| C07K 17/14 | (2006.01) |

(52) U.S. Cl.
CPC ............ *C12N 15/1062* (2013.01); *C07K 17/14* (2013.01); *C12N 15/101* (2013.01); *C12Q 1/6844* (2013.01)

(58) Field of Classification Search
CPC ............ C40B 40/18; C12Q 1/68; G01N 33/52
USPC ........... 506/17, 32; 435/6.1, 91.1, 91.51, 174; 422/430; 536/22.1
See application file for complete search history.

(56) References Cited

U.S. PATENT DOCUMENTS

| | | | |
|---|---|---|---|
| 2008/0312103 A1 | 12/2008 | Nemoto et al. | |
| 2010/0035769 A1 | 2/2010 | Nemoto et al. | |

FOREIGN PATENT DOCUMENTS

| | | | |
|---|---|---|---|
| JP | 2005-245223 A | | 9/2005 |
| JP | 2008-116218 A | | 5/2008 |
| JP | 2008253176 | * | 10/2008 |
| JP | 4318721 B | | 8/2009 |
| JP | 2011-087573 A | | 5/2011 |

OTHER PUBLICATIONS

Machine Translation of JP200825376MT document, 2015, down loaded from the JPO on Jul. 7, 2015, pp. 1-11.*
Mochizuki et al, A pull-down method with a biotinylated bait protein prepared by cell-free translation using a puromycin linker, 2013, Analytical Biochemistry, 434, 93-95.*
Nemoto et al., "In vitro virus: Bonding of mRNA bearing puromycin at the 3'-terminal end to the C-terminal end of its encoded protein on the ribosome in vitro," FEBS Letters, 414: 405-408 (1997).
Yamaguchi et al., "cDNA display: a novel screening method for functional disulfide-rich peptides by solid-phase synthesis and stabilization of mRNA-protein fusions," Nucleic Acids Research, 37: e108 (2009).
International Search Report issued in corresponding International Patent Application No. PCT/JP2012/078321 dated Jan. 8, 2013.
Written Opinion issued in corresponding International Patent Application No. PCT/JP2012/078321 dated Jan. 8, 2013.

* cited by examiner

*Primary Examiner* — Narayan Bhat
(74) *Attorney, Agent, or Firm* — Morgan, Lewis & Bockius LLP

(57) ABSTRACT

A protein-immobilizing solid phase is a protein-immobilizing solid phase comprising an mRNA-nucleic acid linker-protein complex, obtained by linking the mRNA and the protein encoded by that mRNA through the nucleic acid linker, immobilized on the solid phase, wherein the nucleic acid linker has a photocleavage site and a solid phase binding site.

21 Claims, 12 Drawing Sheets

(A)

A region measuring 19.7 × 19.7 μm² in a solution was
irradiated with 377 nm laser for 30 seconds (1.39 J/mm²)

Nitrobenzyl group present

Nitrobenzyl group absent (B)

(A)

(B)

(C)

PROTEIN-IMMOBILIZING SOLID PHASE, POLYNUCLEOTIDE-IMMOBILIZING SOLID PHASE, AND NUCLEIC ACID RECOVERY METHOD

This is a Continuation Application of International Application No. PCT/JP2012/078321, filed Nov. 1, 2012, which claims priority to Japanese Patent Application No. 2011-242789 filed in Japan on Nov. 4, 2011. The contents of the aforementioned applications are incorporated herein by reference.

Sequence Listing Submission Via EFS-Web

A computer readable text file, entitled "SequenceListing.txt," created on or about May 30, 2014 with a file size of about 4 kb contains the sequence listing for this application and is hereby incorporated by reference in its entirety.

BACKGROUND

The present invention relates to a protein-immobilizing solid phase, a polynucleotide-immobilizing solid phase, and a nucleic acid recovery method.

New functional proteins are expected to contribute to various applications in the field of biotechnology, such as in pharmaceuticals, detergents, food processing, reagents for research and development, clinical analyses as well as bioenergy and biosensors.

Although protein engineering techniques, consisting of using human intellect to design proteins based on protein structural information, have been primarily used when acquiring new functional proteins, since screening methods more efficient than those used in the past are required to acquire more useful proteins, expectations are being placed on molecular evolutionary engineering techniques that consist of randomly repeating modification and screening of protein molecular structure.

The cDNA display method, which is a type of molecular evolutionary engineering technique, is a method for associating genotype and phenotype, and consists of the use of a nucleic acid linker to link a protein (phenotype) with mRNA encoding the protein and reverse-transcribed cDNA (genotype). Since the mRNA/cDNA-protein linkage structure is extremely stable, screening can be carried out in various environments by using this nucleic acid linker.

The cDNA display method is characterized by the presence of puromycin in a nucleic acid linker that links a protein with a polynucleotide that encodes that protein (see Japanese Patent No. 4318721).

Puromycin is a protein synthesis inhibitor having a structure that resembles the 3'-terminal of aminoacyl-tRNA, and under prescribed conditions, specifically covalently bonds to the C-terminal of protein during elongation on a ribosome.

Methods for screening useful proteins using the cDNA display method consist of the series of steps described below.

First, a nucleic acid linker containing puromycin is coupled to mRNA, protein is synthesized from the mRNA using a cell-free translation system, and the synthesized protein and mRNA encoding that protein are linked through puromycin to form a complex (mRNA-nucleic acid linker-protein complex) (see Nemoto, et al., FEBS Lett., Vol. 414, pp. 405-408, 1997).

Next, a library of this mRNA-nucleic acid linker-protein complex is prepared, the prepared mRNA-nucleic acid linker-protein complex is reverse-transcribed with reverse transcriptase to synthesize cDNA, and this synthesized cDNA is used to prepare an mRNA/cDNA-nucleic acid linker-protein complex library, followed by selecting a protein having a desired function. The protein can be identified by analyzing the base sequence of the cDNA in the selected mRNA/cDNA-nucleic acid linker-protein complex. Reverse transcription may also be carried out prior to protein selection (see Yamaguchi, et al., Nucleic Acids Res., Vol. 37, p. e108, 2009).

A protein array, in which a library of the aforementioned mRNA (or mRNA/cDNA)-nucleic acid linker-protein complex is immobilized on a substrate, is useful as a tool for acquiring functional protein in a short period of time by comprehensive analysis (see Japanese Unexamined Patent Application, First Publication No. 2008-116218).

SUMMARY

In the case of molecular evolutionary engineering techniques, after screening for a useful protein using a solid-phase carrier or solid-phase substrate on which is immobilized a protein comprising the aforementioned protein array, it is necessary to recover mRNA or cDNA (genotype) associated with the protein (phenotype) from the solid-phase carrier or solid-phase substrate.

However, it is not easy to selectively and efficiently recover the mRNA or cDNA associated with the useful protein from the solid-phase carrier or solid-phase substrate.

As a result of conducting extensive studies, the inventors of the present invention found that problems can be solved by introducing a photocleavage site or cleavage site in a nucleic acid linker. Embodiments of the present invention provide that described in the following (1) to (14). Furthermore, in this application and in the claims, the term "photocleavage site" refers to a site that is cleaved by light, and this term may also be substituted with "cleavage site" in the case the site is cleaved by other physical or chemical energy. In addition, the term "photoirradiation" may also be substituted with "action by physical or chemical energy" for cleaving a "cleavage site".

(1) The protein-immobilizing solid phase in one embodiment of the present invention is a protein-immobilizing solid phase comprising an mRNA-nucleic acid linker-protein complex, obtained by linking mRNA and a protein encoded by that mRNA through a nucleic acid linker, immobilized on a solid phase, wherein the nucleic acid linker has a photocleavage site and a solid phase binding site.

(2) The protein-immobilizing solid phase in one embodiment of the present invention is a protein-immobilizing solid phase comprising an mRNA/cDNA-nucleic acid linker-protein complex, obtained by linking mRNA/cDNA, composed of mRNA and cDNA complementary to the mRNA, and a protein encoded by that mRNA through a nucleic acid linker, immobilized on a solid phase, wherein the nucleic acid linker has a photocleavage site and a solid phase binding site.

(3) In the protein-immobilizing solid phase in one embodiment of the present invention, the aforementioned nucleic acid linker can be composed of one 3'-terminal region and two branched 5'-terminal regions, the aforementioned 3'-terminal region can comprise a single-stranded polynucleotide segment able to hybridize with the sequence on the 3'-terminal side of the aforementioned mRNA and an arm segment branched from the aforementioned single-stranded polynucleotide segment and having a linking segment with the aforementioned protein on the terminal thereof, one of the two 5'-terminal regions can have a bonding site with the 3'-terminal of the aforementioned mRNA, and the other of the two 5'-terminal regions can have a photocleavage site and a solid phase binding site on the 5'-terminal.

(4) In the protein-immobilizing solid phase in one embodiment of the present invention, the aforementioned nucleic acid linker can be composed of one 3'-terminal region and one 5'-terminal region, the aforementioned 3'-terminal region can comprise a single-stranded polynucleotide segment able to hybridize with the sequence on the 3'-terminal side of the aforementioned mRNA and an arm segment that has a first photocleavage site on the 5'-terminal side, is branched from the aforementioned single-stranded polynucleotide segment, and has a linking segment with the aforementioned protein on the terminal thereof, and the aforementioned 5'-terminal region can have, in order starting from the 5'-terminal side, a bonding site with the 3'-terminal of the aforementioned mRNA, a second photocleavage site, and a solid phase binding site branched off from between the aforementioned first photocleavage site and the aforementioned second cleavage site.

(5) In the protein-immobilizing solid phase in one embodiment of the present invention, the aforementioned protein linking segment can have puromycin, a 3'-N-aminoacyl puromycin aminonucleoside or 3'-N-aminoacyl adenosine aminonucleoside bound to the end of the aforementioned arm segment.

(6) The polynucleotide-immobilizing solid phase in one embodiment of the present invention is a polynucleotide-immobilizing solid phase comprising a polynucleotide-nucleic acid linker complex, obtained by linking a polynucleotide and a nucleic acid linker, immobilized on a solid phase, wherein the nucleic acid linker has a photocleavage site and a solid phase binding site.

(7) In the polynucleotide-immobilizing solid phase in one embodiment of the present invention, the aforementioned nucleic acid linker can be composed of one 3'-terminal region and two branched 5'-terminal regions, the aforementioned 3'-terminal region can comprise a single-stranded polynucleotide segment able to hybridize with the sequence on the 3'-terminal side of the aforementioned polynucleotide, one of the two 5'-terminal regions can have a bonding site with the 3'-terminal of the aforementioned polynucleotide, and the other of the two 5'-terminal regions can have a photocleavage site and a solid phase binding site on the 5'-terminal.

(8) In the polynucleotide-immobilizing solid phase in one embodiment of the present invention, the aforementioned nucleic acid linker can be composed of one 3'-terminal region and one 5'-terminal region, the aforementioned 3'-terminal region can have a single-stranded polynucleotide segment able to hybridize with the sequence on the 3'-terminal side of the aforementioned polynucleotide and a first photocleavage site on the 5'-terminal side, and the aforementioned 5'-terminal region can have, in order starting from the 5'-terminal side, a bonding site with the 3'-terminal of the aforementioned polynucleotide, a second photocleavage site, and a solid phase binding site branched off from between the aforementioned first photocleavage site and the aforementioned second cleavage site.

(9) The nucleic acid recovery method in one embodiment of the present invention has a step for recovering an mRNA-protein complex, an mRNA/cDNA-protein complex or a polynucleotide using the previously described immobilizing solid phase by cleaving the aforementioned nucleic acid linker at a photocleavage site of the aforementioned nucleic acid linker by photoirradiating the immobilizing solid phase.

(10) The protein-immobilizing solid phase in one embodiment of the present invention is a protein-immobilizing solid phase comprising an mRNA-nucleic acid linker-protein complex, obtained by linking mRNA and a protein encoded by that mRNA through a nucleic acid linker, immobilized on a solid phase, wherein the nucleic acid linker has a cleavage site and a solid phase binding site.

(11) In the protein-immobilizing solid phase in one embodiment of the present invention, the aforementioned protein can compose any one of an enzyme, antibody, antigen, aptamer and peptide.

(12) The protein-immobilizing solid phase in one embodiment of the present invention is a polynucleotide-immobilizing solid phase comprising a polynucleotide-nucleic acid linker complex, obtained by linking a polynucleotide and a nucleic acid linker, immobilized on a solid phase, wherein the nucleic acid linker has a cleavage site and a solid phase binding site.

(13) The nucleic acid recovery method in one embodiment of the present invention has a step for recovering an mRNA-protein complex, an mRNA/cDNA-protein complex or a polynucleotide using the previously described immobilizing solid phase by cleaving the aforementioned nucleic acid linker at a cleavage site of the aforementioned nucleic acid linker.

(14) In the polynucleotide-immobilizing solid phase in one embodiment of the present invention, the aforementioned nucleic acid linker can be composed of one 3'-terminal region and two branched 5'-terminal regions, the aforementioned 3'-terminal region can comprise a single-stranded polynucleotide segment able to hybridize with the sequence on the 3'-terminal side of the aforementioned polynucleotide, one of the two 5'-terminal regions can have a bonding site with the 3'-terminal of the aforementioned polynucleotide, and the other of the two 5'-terminal regions can have a cleavage site and a solid phase binding site on the 5'-terminal.

DETAILED DESCRIPTION

Protein-Immobilizing Solid Phase

First Embodiment

The protein-immobilizing solid phase of the present embodiment is a protein-immobilizing solid phase comprising an mRNA-nucleic acid linker-protein complex, obtained by linking mRNA and a protein encoded by that mRNA through a nucleic acid linker, immobilized on a solid phase, wherein the nucleic acid linker has a cleavage site (such as a photocleavage site) and a solid phase binding site.

Figure 1:
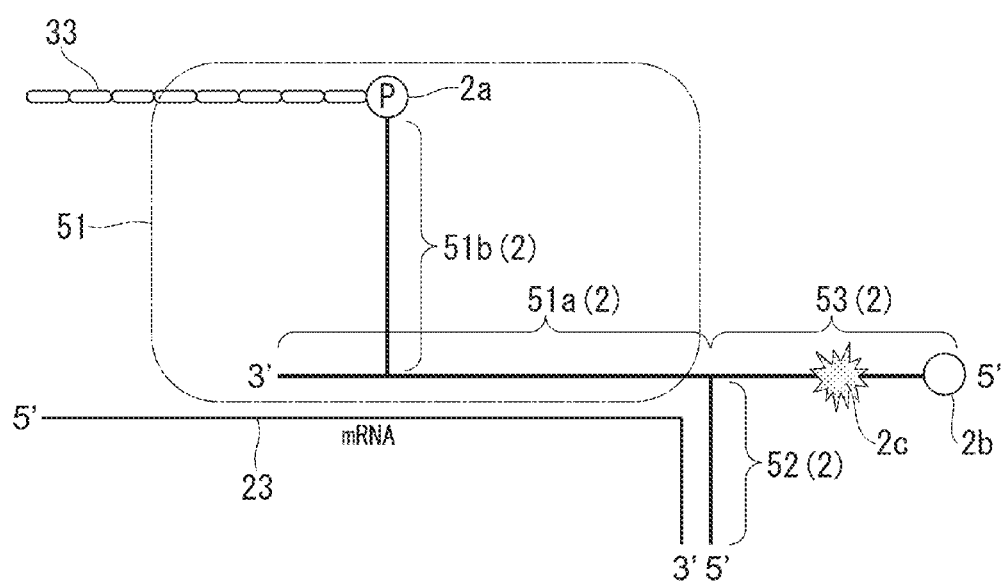
FIG. 1 is a drawing showing one aspect of a nucleic acid linker used in one embodiment.

First, an explanation is provided of a structure of an mRNA 23-nucleic acid linker 2-protein 33 complex used in the present embodiment with reference to FIG. 1.

(Nucleic Acid Linker)

The nucleic acid linker 2 used in the present embodiment is a linker for linking the mRNA 23 and the protein 33 encoded thereby.

In FIG. 1, P indicates puromycin.

The nucleic acid linker 2 is composed of one 3'-terminal region 51 and two branched 5'-terminal regions (one region 52 and other region 53).

The 3'-terminal region 51 comprises a single-stranded polynucleotide segment 51a, which is able to hybridize with the sequence on the 3'-terminal side of the mRNA 23 that encodes the protein 33 to be screened, and an arm segment 51b, which branches from the single-stranded polynucleotide segment 51a and has a linking segment 2a with the protein 33 on the terminal thereof.

The single-stranded polynucleotide segment 51a may be DNA or a nucleic acid derivative such as a polynucleopeptide (PNA), and is preferably modified DNA imparted with nuclease resistance. Any modified DNA known in the art may be used as modified DNA, examples of which include DNA having an internucleoside bond such as a phosphorothioate bond and DNA having a sugar modification such as 2'-fluoro, 2'-O-alkyl.

The arm segment 51b functions as a spacer that maintains a desired distance between the mRNA 23 and the protein linking segment 2a. The 5'-terminal of the arm segment 51b bonds to the single-stranded polynucleotide segment 51a at a location on the 3'-terminal side of the single-stranded polynucleotide segment 51a, while the 3'-terminal of the arm segment 51b has the protein linking segment 2a.

Linking between the single-stranded polynucleotide segment 51a and the arm segment 51b is carried out by crosslinking between a modified nucleotide present at a linking location on the single-stranded polynucleotide segment 51a (such as a nucleotide in which an amino group is introduced into a base moiety through a spacer) and a modified nucleotide present on the end of the arm segment 51b (such as a nucleotide having a thiol on the 5'-terminal thereof) using a bifunctional reagent.

As will be subsequently described, in the case mRNA encoding a protein to be screened is required to be reverse-transcribed, the 5'-terminal of the arm segment 51b preferably forms a T-shaped structure by bonding with the single-stranded polynucleotide segment 51a at a location several bases towards the 5'-side from the 3'-terminal of the single-stranded polynucleotide segment 51a. This is because the 3'-terminal of the single-stranded polynucleotide segment 51a functions as a primer during reverse transcription.

The single-stranded polynucleotide segment 51a or the arm segment 51b, excluding the terminals thereof, may be labeled using a labeling substance. The labeling substance is suitably selected from a fluorescent dye or radioactive substance and the like.

The linking segment 2a with the protein 33 is present on the 3'-terminal of the arm segment 51b. The protein linking segment 2a refers to a structure having the property of specifically bonding to the C-terminal of the protein 33 during elongation on a ribosome under prescribed conditions, and a typical example thereof is puromycin.

Puromycin is a protein synthesis inhibitor having a structure that resembles the 3'-terminal of aminoacyl-tRNA. Any arbitrary substance can be used for the linking segment 2a with the protein 33 provided it has a function that allows it to specifically bond to the C-terminal of the protein 33 during elongation, and puromycin derivatives such as 3'-N-aminoacyl puromycin aminonucleoside (PANS-amino acid) or 3'-N-aminoacyl adenosine aminonucleoside (AANS-amino acid) can be used.

Examples of PANS-amino acids include PANS-Gly in which the amino acid moiety is glycine, PANS-Val in which it is valine, PANS-Ala in which it is alanine, and PANS-amino acid mixtures in which the amino acid moieties correspond to each amino acid in all amino acids.

Examples of AANS-amino acids include AANS-Gly, in which the amino acid moiety is glycine, AANS-Val in which it is valine, AANS-Ala in which it is alanine, and AANS-amino acid mixtures in which the amino acid moieties correspond to each amino acid in all amino acids.

Examples of amino acyl-tRNA 3'-terminal analogues able to be used preferably other than puromycin include ribocytidyl puromycin (rCpPur), deoxycytidyl puromycin (dCpPur) and deoxyuridyl puromycin (dUpPur).

The arm segment 51b may be composed of nucleic acids or nucleic acid derivatives provided it functions as a spacer, and may be composed of a polymer such as polyethylene glycol.

Modifications for enhancing the stability of puromycin or a label for detecting a complex may be further added to the arm segment 51b.

The 5'-terminal region is branched into two regions consisting of one region 52 and another region 53. The one region 52 preferably forms a T-shaped structure by branching from the boundary between the single-stranded polynucleotide segment 51a of the 3'-terminal region 51 and the other region 53. A modified nucleotide amidite or branching phosphate group amidite capable of synthesizing branched chains from a base moiety through a spacer is used to synthesize this branched segment in the form of the one region 52.

The 5'-terminal of the one region 52 is preferably ligated with the 3'-terminal of the mRNA 23 in order to strengthen the bond with the single-stranded polynucleotide segment 51a able to hybridize with the mRNA 23.

The other region 53 of the nucleic acid linker 2 of the present embodiment contains a photocleavage site 2c. The mRNA 23 associated with the protein 33 can be recovered from a solid phase due to the presence of the photocleavage site 2c.

A photocleavage site refers to a group having the property of being cleaved when irradiated with light such as ultraviolet light. Examples of products using this group include PC Linker Phosphoramidite (Glen Research) and a composition for nucleic acid photocleavage containing fullerene (Composition for Nucleic Acid Photocleavage: Japanese Unexamined Patent Application, First Publication No. 2005-245223).

A commercially available product in the art or any known group, such as a nitrobenzyl group, may be used as a photocleavage site.

In addition, the other region 53 of the nucleic acid linker 2 of the present embodiment contains, for example, a single-stranded nucleic acid cleaving enzyme cleavage site. A single-stranded nucleic acid cleaving enzyme cleavage site refers to a nucleic acid group able to be cleaved by a single-stranded nucleic acid cleaving enzyme such as deoxyribonuclease or ribonuclease, and includes nucleotides and derivatives thereof, such as deoxyinosine recognized by endonuclease V.

The other region 53 of the nucleic acid linker 2 of the present embodiment has a solid phase binding site 2b on the 5'-terminal thereof.

In addition to methods utilizing avidin-biotin bonding, a method consisting of modifying the nucleic acid linker 2 with a functional group such as an amino group, formyl group or SH group and treating the surface of the solid phase with a silane coupling agent having an amino group, formyl group or epoxy group and the like, or a method that utilizes gold-thiol bonding, can be preferably used for immobilization of the nucleic acid linker 2, while a method that utilizes avidin-biotin bonding is particularly preferable.

Figure 2:
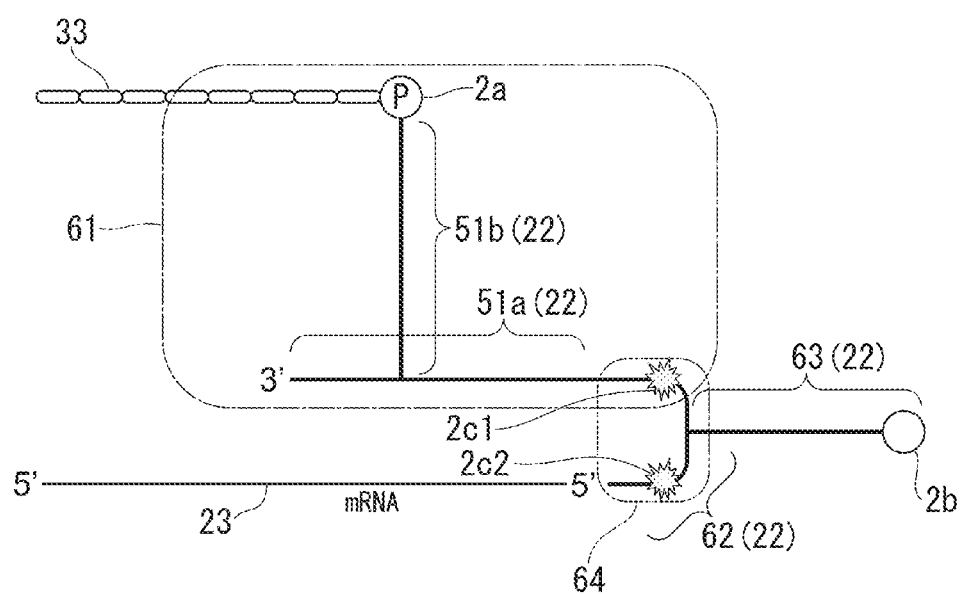
FIG. 2 is a drawing showing one aspect of a nucleic acid linker used in one embodiment.

In addition, in the present embodiment, a nucleic acid linker 22 shown in FIG. 2 may be used as a nucleic acid linker. In FIG. 2, the same reference symbols are used to indicate those constituent elements that are the same as those shown in the schematic drawing of the nucleic acid linker 2 of FIG. 1, and an explanation thereof is omitted.

The nucleic acid linker 22 is composed of one 3'-terminal region 61 and one 5'-terminal region 62.

The 5'-terminal region 62 and the 3'-terminal region 61 form a loop region 64.

The 3'-terminal region 61 contains a first photocleavage site 2c1 on the 5'-terminal side, while the 5'-terminal region 62 contains a second photocleavage site 2c2.

The 5'-terminal region 62 has, in order starting from the 5'-terminal side, a bonding site with the 3'-terminal of the mRNA 23, the second photocleavage site 2c2, and the solid phase binding site 2b branched off from between the first photocleavage site 2c1 and the second photocleavage site 2c2. A branched region 63, having the solid phase binding site 2b on the end thereof, preferably forms a T-shaped structure by branching from the loop region 64. A modified nucleotide amidite or branching phosphate group amidite capable of synthesizing branched chains from a base moiety through a spacer, or a nucleotide amidite, in which the solid phase binding site has been modified to a base moiety through a spacer, is used to synthesize the branched region 63.

The 5'-terminal of the 5'-terminal region 62 is preferably ligated with the 3'-terminal of the mRNA 23 to strengthen the bond with the single-stranded polynucleotide segment 51a able to hybridize with the mRNA 23.

(mRNA-Nucleic Acid Linker-Protein Complex)

Next, an mRNA 23-nucleic acid linker 2-protein 33 complex is produced using the nucleic acid linker 2.

A method for producing the mRNA 23-nucleic acid linker 2-protein 33 complex comprises:

(a) a step for annealing the mRNA 23 and the nucleic acid linker 2, (b) a step for ligating the 3'-terminal of the mRNA 23 and the 5'-terminal of the nucleic acid linker 2, and (c) a step for preparing the mRNA 23-nucleic acid linker 2-protein 33 complex, in which the C-terminal of the protein 33 is bound to the protein linking segment 2a of the nucleic acid linker 2, by synthesizing the protein 33 from the mRNA 23 using a cell-free protein translation system.

The following provides an explanation of each step.

In step (a), the mRNA 23 and the nucleic acid linker 2 are annealed. First, an explanation is provided of preparation of the mRNA 23 used in step (a).

The mRNA 23 is obtained by preparing DNA encoding a protein to be screened and transcribing with RNA polymerase. An example of RNA polymerase is T7 RNA polymerase.

An arbitrary DNA or DNA library desired to be investigated with respect to bonding with a target molecule can be used for the aforementioned DNA. Examples thereof that can be used include a cDNA library obtained from a sample tissue, a DNA library obtained by random sequence synthesis, and a DNA library obtained by partial sequence mutation.

The 3'-side of mRNA following transcription is designed so as to hybridize with the single-stranded polynucleotide segment 51a of the nucleic acid linker 2 by inserting a common tag sequence into the 3'-terminal of the DNA prior to transcription.

Next, the 3'-terminal region of the mRNA 23 and the single-stranded polynucleotide segment 51a of the nucleic acid linker 2 are annealed. For example, the mRNA 23 can be reliably hybridized with the nucleic acid linker 2 by denaturing the mRNA 23 by heating to 90° C. followed by cooling to 25° C. over the course of 15 minutes.

Next, in step (b), the 3'-terminal of the mRNA 23 and one of the 5'-terminal regions of the nucleic acid linker 2 are ligated. During ligation, it is necessary to phosphorylate the 5'-terminal of the nucleic acid linker 2 using an enzyme such as T4 polynucleotide kinase. An RNA ligase is preferably used for the enzyme used for ligation, and an example thereof is T4 RNA ligase.

Next, in step (c), the mRNA 23-nucleic acid linker 2-protein 33 complex is prepared, in which the C-terminal of the protein 33 is bound to the protein linker segment 2a of the nucleic acid linker 2, by synthesizing the protein 33 from the mRNA 23 using a cell-free protein translation system.

A cell-free protein translation system refers to a protein translation system composed of components having the ability to synthesize protein that have been extracted from suitable cells, and elements required for translation are contained in this system, examples of which include ribosomes, translation initiation factors, translation elongation factors, dissociating factors and aminoacyl-tRNA synthetase. Examples of such protein translation systems include *Escherichia coli* extract, rabbit reticulocyte extract and wheat germ extract.

Moreover, another example of a cell-free protein translation system is a reconstituted cell-free protein synthesis system composed only of factors in which elements required for translation have been independently purified. Reconstituted cell-free protein synthesis systems are able to enhance translation efficiency since they are able to more easily prevent contamination by nucleases or proteases than in the case of using conventional cell extracts.

The mRNA 23-nucleic acid linker 2-protein 33 complex is produced by using such a system.

A protein-immobilizing solid phase is produced by immobilizing the aforementioned mRNA 23-nucleic acid linker 2-protein 33 complex on a solid phase. There are no particular limitations on the immobilization method, and the mRNA 23-nucleic acid linker 2-protein 33 complex may be immobilized after translation as previously described, or the mRNA 23-nucleic acid linker 2-protein 33 complex may be produced on a solid phase by translating the mRNA 23-nucleic acid linker 2 complex prior to translation after immobilizing on a solid phase.

Preferable examples of the solid phase include a substrate or carrier beads.

(Protein Array)

A protein array is produced by immobilizing the aforementioned mRNA 23-nucleic acid linker 2-protein 33 complex on a substrate. Examples of substrates used include a glass substrate, silicon substrate, plastic substrate and metal substrate. Since a solid phase binding site is provided in the nucleic acid linker 2 of the mRNA 23-nucleic acid linker 2-protein 33 complex on the 5'-terminal thereof, the mRNA 23-nucleic acid linker 2-protein 33 complex is immobilized on a substrate by utilizing binding between that solid phase binding site and a solid phase binding site recognition site bound to the substrate.

In addition to the use of avidin-biotin bonding, examples of methods that can be used to immobilize the nucleic acid linker 2 when using a combination of a solid phase binding site and a solid phase binding site recognition site include a method consisting of modifying the nucleic acid linker 2 with a functional group such as an amino group, formyl group or SH group and treating the surface of the solid phase with a silane coupling agent having an amino group, formyl group or epoxy group and the like, and a method that utilizes gold-thiol bonding, while a method that utilizes avidin-biotin bonding is particularly preferable.

(Protein-Bound Beads)

Protein-bound beads are produced by immobilizing the aforementioned mRNA 23-nucleic acid linker 2-protein 33 complex on carrier beads. Examples of carrier beads used include magnetic beads, gold nanoparticles, agarose beads and plastic beads, while magnetic beads are preferable since they facilitate handling using magnetism. A protein array can be composed by using protein-bound beads and arranging in reaction vessels in a bead array substrate having a plurality of reaction vessels arranged therein.

Similar to when using a combination of a solid phase binding site and solid phase binding site recognition site in a protein array, examples of methods, in addition to the use of avidin-biotin bonding, that can be used to immobilize the mRNA 23-nucleic acid linker 2-protein 33 complex include a method consisting of modifying the nucleic acid linker 2 with a functional group such as an amino group, formyl group or SH group and treating the surface of the carrier beads with a silane coupling agent having an amino group, formyl group or epoxy group and the like, and a method that utilizes gold-thiol bonding, while a method that utilizes avidin-biotin bonding is particularly preferable.

According to the protein-immobilizing solid phase of the present embodiment, since the nucleic acid linker 2 that composes the mRNA 23-nucleic acid linker 2-protein 33 complex has the other region 53, distance can be created between the solid phase and the photocleavage site 2c by suitably extending the base sequence of the 5'-terminal that composes the other region 53.

For example, in the case of using the nucleic acid linker 2 having a nitrobenzyl group for the photocleavage site 2c and using a gold substrate for the solid phase, there is the risk of the gold substrate absorbing light energy required to cleave the nitrobenzyl group if the distance between the gold substrate and the nitrobenzyl group is short. In the present embodiment, this risk is eliminated, thereby making it possible to efficiently recover the mRNA 23 associated with the protein 33 by efficiently cleaving the nucleic acid linker 2 by photoirradiation.

Second Embodiment

The protein-immobilizing solid phase of the present embodiment is a protein-immobilizing solid phase comprising an mRNA/cDNA-nucleic acid linker-protein complex, obtained by linking mRNA/cDNA, composed of mRNA and cDNA complementary to the mRNA, and a protein encoded by that mRNA through a nucleic acid linker, immobilized on a solid phase, wherein the nucleic acid linker has a cleavage site (such as a photocleavage site) and a solid phase binding site.

Figure 3:
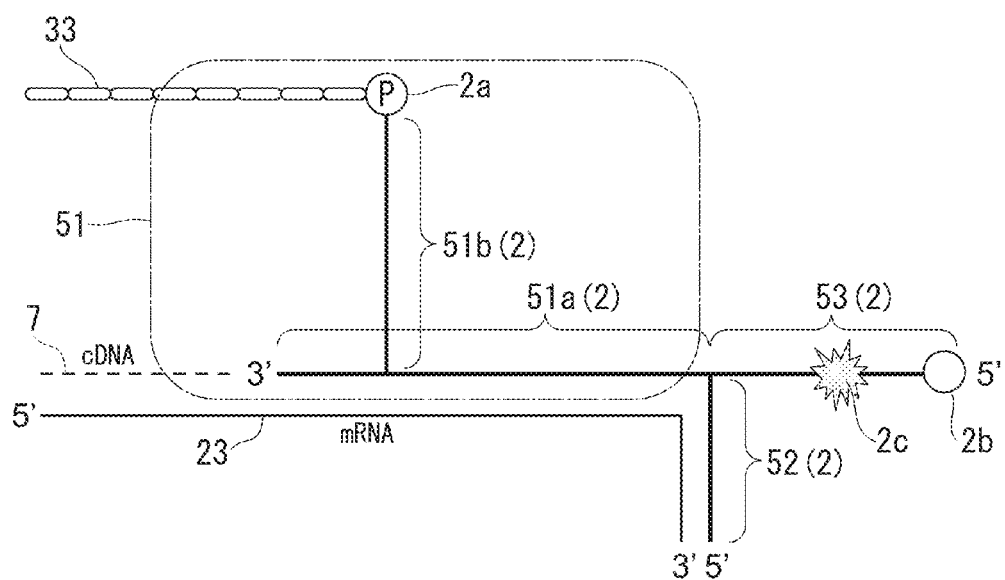
FIG. 3 is a drawing showing one aspect of a nucleic acid linker used in one embodiment.

The following provides an explanation of an mRNA 23/cDNA 7-nucleic acid linker 2 complex used in the present embodiment with reference to FIG. 3.

In FIG. 3, the same reference symbols are used to indicate those constituent elements that are the same as those explained in the first embodiment, and an explanation thereof is omitted.

(mRNA/cDNA-Nucleic Acid Linker-Protein Complex)

A method for producing the mRNA/cDNA-nucleic acid linker-protein complex has a step (d) in addition to the steps comprising the previously described method for producing an mRNA-nucleic acid linker-protein complex.

Step (d) is a step for preparing the mRNA 23/cDNA 7-nucleic acid linker 2 complex by subjecting the mRNA 23-nucleic acid linker 2-protein 33 complex to a reverse transcription reaction.

In step (d), a known reverse transcriptase is used for the reverse transcriptase used in reverse transcription, and an example thereof is reverse transcriptase derived from Moloney murine leukemia virus.

Reverse transcribed cDNA 7 forms a hybrid with the mRNA 23 of the mRNA 23-nucleic acid linker 2-protein 33 complex. In addition to the mRNA 23 in the mRNA 23-nucleic acid linker 2-protein 33 complex being more easily degradable than cDNA, since it also has a high possibility of non-specifically interacting as aptamers, in the case of analyzing protein interaction, it is preferable to prepare this type of mRNA/cDNA-nucleic acid linker-protein complex.

In addition, it is also essential to prepare this complex in order to analyze cDNA that encodes a protein which has been found to be useful as a result of screening.

According to the protein-immobilizing solid phase of the present embodiment, the cDNA 7 associated with the protein 33 can be efficiently recovered by efficiently cleaving the nucleic acid linker 2 by photoirradiation.

<<Polynucleotide-Immobilizing Solid Phase>>

The polynucleotide-immobilizing solid phase of the present embodiment is a polynucleotide-immobilizing solid phase comprising a polynucleotide-nucleic acid linker complex, obtained by linking DNA or RNA and a nucleic acid linker, immobilized on a solid phase, wherein the nucleic acid linker has a cleavage site (such as a photocleavage site) and a solid phase binding site.

Figure 4:
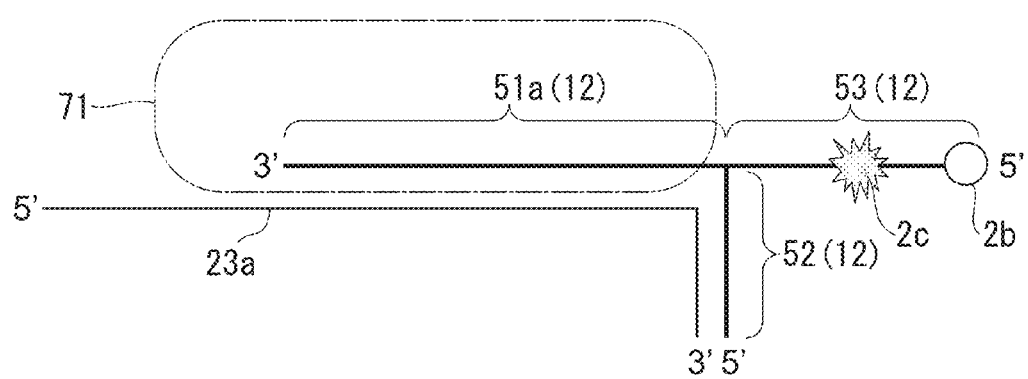
FIG. 4 is a drawing showing one aspect of a nucleic acid linker used in one embodiment.

First, an explanation is provided of a structure of a polynucleotide 23a-nuclear acid linker 12 complex used in the present embodiment with reference to FIG. 4. In FIG. 4, the same reference symbols are used to indicate those constituent elements that are the same as those indicated in the embodiments of the protein-immobilizing solid phase, and an explanation thereof is omitted.

(Nucleic Acid Linker)

The nucleic acid linker 12 used in the present embodiment is a linker that links with the polynucleotide 23a.

Similar to that indicated in the embodiments of the protein-immobilizing solid phase, the nucleic acid linker 12 is composed of one 3'-terminal region 71 and two branched 5'-terminal regions (consisting of one region 52 and another region 53). The 3'-terminal region 71 contains the single-stranded polynucleotide segment 51a able to hybridize with the sequence on the 3'-terminal side of the polynucleotide 23a to be screened.

Since the polynucleotide 23a to be screened can be presumed to be a functional polynucleotide such as a ribozyme, deoxyribozyme, RNA aptamer or DNA aptamer, in the present embodiment, the polynucleotide 23a able to be hybridized by the single-stranded polynucleotide segment 51a is not limited to mRNA. In addition, the 3'-terminal region 71 is not required to contain an arm segment having a protein linking segment on the end thereof.

Figure 5:
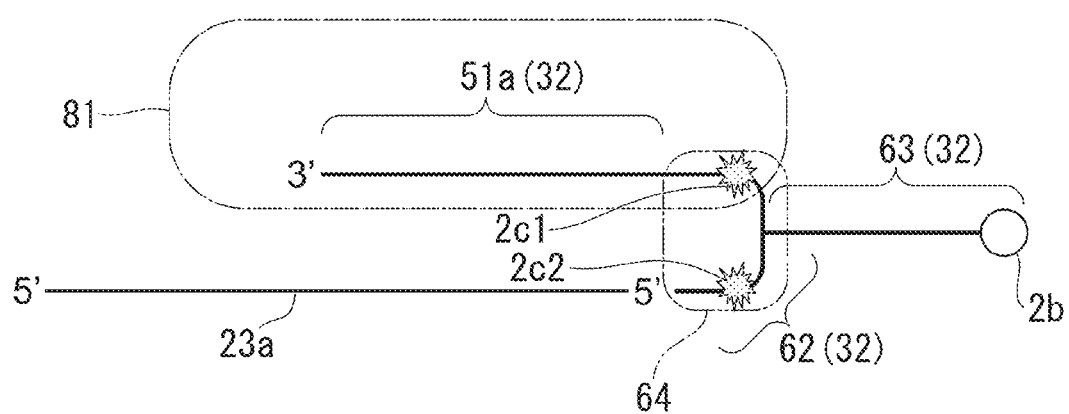
FIG. 5 is a drawing showing one aspect of a nucleic acid linker used in one embodiment.

In addition, in the present embodiment, a nucleic acid linker 32 shown in FIG. 5 may be used as a nucleic acid linker. In FIG. 5, the same reference symbols are used to indicate those constituent elements that are the same as those shown in the schematic drawing of the nucleic acid linker 12 of FIG. 4, and an explanation thereof is omitted.

The nucleic acid linker 32 is composed of one 3'-terminal region 81 and one 5'-terminal region 62.

The 5'-terminal region 62 and the 3'-terminal region 81 form the loop region 64.

The 3'-terminal region 81 contains the first photocleavage site 2c1 on the 5'-terminal side thereof, and the 5'-terminal region 62 contains the second photocleavage site 2c2.

The 5'-terminal region 62 has, in order starting from the 5'-terminal side, a bonding site with the 3'-terminal of the polynucleotide 23a, the second photocleavage site 2c2, and the solid phase binding site 2b branched off from between the first photocleavage site 2c1 and the second cleavage site 2c2. The branched region 63, having the solid phase binding site 2b on the end thereof, preferably forms a T-shaped structure by branching from the loop region 64. A modified nucleotide amidite or branching phosphate group amidite capable of synthesizing branched chains from a base moiety through a spacer, or a nucleotide amidite, in which the solid phase binding site has been modified to a base moiety through a spacer, is used to synthesize the branched region 63.

The 5'-terminal of the 5'-terminal region 62 is preferably ligated with the 3'-terminal of the polynucleotide 23a to strengthen the bond with the single-stranded polynucleotide segment 51a able to hybridize with the mRNA 23.

(Polynucleotide-Nucleic Acid Linker Complex)

Next, a polynucleotide 23a-nucleic acid linker 12 complex is produced using the nucleic acid linker 12.

A method for producing the polynucleotide 23a-nucleic acid linker 12 complex comprises:

(a') a step for annealing the polynucleotide 23a and the nucleic acid linker 12, and (b') a step for ligating the 3'-terminal of the polynucleotide 23a and the 5'-terminal of the nucleic acid linker 12.

With the exception of changing the mRNA 23 to the polynucleotide 23a and changing the nucleic acid linker 2 to the nucleic acid linker 12, step (a') and step (b') are the same as step (a) and step (b) in the previously described method for producing the mRNA 23-nucleic acid linker 2-protein 33 complex.

A polynucleotide-immobilizing solid phase is produced by immobilizing the aforementioned polynucleotide 23a-nucleic acid linker 12 complex on a solid phase.

A substrate or carrier beads are preferably used for the solid phase.

(Polynucleotide Microarray)

A polynucleotide microarray is produce by immobilizing the aforementioned polynucleotide 23a-nucleic acid linker 12 complex on a substrate. Examples of substrates used include a glass substrate, silicon substrate, plastic substrate and metal substrate. Since a solid phase binding site is provided in the nucleic acid linker 12 of the polynucleotide 23a-nucleic acid linker 12 complex on the 5'-terminal thereof, the polynucleotide 23a-nucleic acid linker 12 complex is immobilized on a substrate by utilizing binding between that solid phase binding site and a solid phase binding site recognition site bound to the substrate.

Examples of such combinations of a solid phase binding site and solid phase binding site recognition site are the same as those indicated in the embodiments of the protein-immobilizing solid phase, and a method that utilizes avidin-biotin bonding is particularly preferable.

(Polynucleotide-Bound Beads)

Polynucleotide-bound beads are produced by immobilizing the aforementioned polynucleotide 23a-nucleic acid linker 12 complex on carrier beads. Examples of carrier beads used include magnetic beads, gold nanoparticles, agarose beads and plastic beads, while magnetic beads are preferable since they facilitate handling using magnetism. A polynucleotide microarray can be composed by using polynucleotide-bound beads and arranging in reaction vessels in a bead array substrate having a plurality of reaction vessels arranged therein. Similar to when using a combination of a solid phase binding site and solid phase binding site recognition site in a protein array, examples of methods, in addition to the use of avidin-biotin bonding, that can be used to immobilize the polynucleotide 23a-nucleic acid linker 12 complex include a method consisting of modifying the nucleic acid linker 12 with a functional group such as an amino group, formyl group or SH group and treating the surface of the carrier beads with a silane coupling agent having an amino group, formyl group or epoxy group and the like, and a method that utilizes gold-thiol bonding, while a method that utilizes avidin-biotin bonding is particularly preferable.

According to the polynucleotide-immobilizing solid phase of the present embodiment, the polynucleotide 23a can be efficiently recovered as a functional polynucleotide by efficiently cleaving the nucleic acid linker 12 by photoirradiation.

<<Nucleic Acid Recovery Method>>

The nucleic acid recovery method of the present embodiment has a step for recovering an mRNA-protein complex, an mRNA/cDNA-protein complex or a polynucleotide using the previously described immobilizing solid phase by cleaving the aforementioned nucleic acid linker at a cleavage site (such as a photocleavage site) of the aforementioned nucleic acid linker by photoirradiating the immobilizing solid phase.

An mRNA-protein complex, mRNA/cDNA-protein complex or polynucleotide is immobilized through a nucleic acid linker at a spot that has been discovered by carrying out screening using the aforementioned protein-immobilizing solid phase or polynucleotide-immobilizing solid phase. Since the nucleic acid linker has a photocleavage site, the nucleic acid linker is cleaved by photoirradiating a specific spot, thereby separating the mRNA-protein complex, mRNA/cDNA-protein complex or polynucleotide from the spot. A useful protein or useful polynucleotide is then identified by analyzing the base sequences of these nucleic acids.

For example, a cleavage reaction using photoirradiation is superior from the viewpoint of enabling photoirradiation of a microscopic region on the micrometer order. The wavelength of radiated light is preferably 300 nm or longer in consideration of the wavelength at which the nitrobenzyl group used for the photocleavage site of the nucleic acid linker is cleaved, and more preferably 350 nm to 400 nm in consideration of suppressing damage caused by photoirradiation to the nucleic acid targeted for analysis.

For example, the nucleic acid recovery method of the present embodiment preferably has a step for capturing a nucleic acid that has been cleaved and separated by photoirradiation or a nucleic acid cleaving enzyme using a solid phase having a positive charge.

Examples of the solid phase include solid phase carriers and solid phase substrates, and as is indicated in the examples to be subsequently described, a solid phase substrate is preferable from the viewpoint of being able to be used as a cover when carrying out a nucleic acid cleavage reaction by photoirradiation.

Examples of solid phase carriers include magnetic beads, gold nanoparticles, agarose beads and plastic beads.

Examples of solid phase substrates include a glass substrate, silicon substrate, plastic substrate and metal substrate.

These solid phases are able to capture nucleic acids having a negative charge as a result of having a positive charge. An example of a means for controlling that charge is a method consisting of introducing a functional group having a positive charge onto the surface of the solid phase by chemically modifying the solid phase.

Examples of functional groups having a positive charge include monoalkylamino groups such as an amino group, methylamino group or ethylamino group; dialkylamino groups such as a dimethylamino group, diethylamino group or dimethylaminoethyl group; an imino group and a guanidino group, and an amino group is preferable.

For example, in the case of using a glass substrate for the solid phase, the surface thereof can be easily treated by using a silane coupling agent having an amino group.

In addition, another example is a method consisting of enhancing electrostatic interaction between a solid phase and nucleic acid by controlling the solid phase so as to have a positive zeta potential with an electrical control means.

After having captured a nucleic acid in this manner, the captured nucleic acid can be easily released by switching the charge of the surface of the solid phase from a positive charge to a negative charge.

Examples of methods used to switch charge include a method consisting of changing the pH of the solution using a phosphate buffer solution, a method consisting of eluting the captured nucleic acid using a solution of a molecule having a nucleic acid-like structure, and a method consisting of controlling the solid phase to have a negative zeta potential with an electrical control means.

According to the nucleic acid recovery method of the present embodiment, mRNA, cDNA or a useful polynucleotide can be selectively and efficiently recovered from a solid phase having a useful protein or useful polynucleotide immobilized thereon.

Although the following provides an explanation of the present invention using examples thereof, the present invention is not limited to the following examples.

EXAMPLES

Synthesis of Nucleic Acid Linker 1-1 Materials

Synthesis of the three types of DNA oligomers indicated below was commissioned to JBioS, and the DNA oligomers were synthesized in accordance with the phosphoramidite method using an automated nucleic acid synthesizer.

(1) PC-Branch-Thiol Segment (SEQ ID NO: 9)
[Sequence: 5'-(HO—$C_6H_{12}$—SS—$C_6H_{12}$)-TTTTTTTTTTTTT

TTTTTTTTTTTTTTT-(PC)-TTT(C—CCC-5')-X1-(T—$NH_2$)-

CCT-3']

X1 represents the sequence indicated below.

(SEQ ID NO: 1, 15 mer)
CCCCGCCGCCCCCG (2) PC-Branch-Biotin Segment (SEQ ID NO: 10)
[Sequence: 5'-(B)-TTTTTTTTTTTTTTTTTTT-(PC)-

TTT(C—CCC-5')-X1-(T—$NH_2$)-CCT-3']

X1 is as indicated above.

(3) Puromycin Segment

[Sequence: 5'-(HO—$C_6H_{12}$—SS—$C_6H_{12}$)-TCT-(spc18)-

(spc18)-(spc18)-CC-(Puromycin)-3']

Here, (HO—$C_6H_{12}$—SS—$C_6H_{12}$) represents that synthesized using (1-O-dimethyoxytrityl-hexyl-disulfide, 1'-[(2-cyanoethyl)-(N,N-diisopropyl)]-phosphoramidite (trade name: Thiol-Modifier C6 S-S, Glen Research).

(PC) represents that synthesized using [4-(4,4'-dimethoxytrityloxy)butyramidomethyl]-1-(2-nitrophenyl)-ethyl]-2-cyanoethyl-(N,N-diisopropyl)-phosphoramidite (trade name: PC Spacer Phosphoramidite, Glen Research).

(C-CCC-5') represents that obtained by condensing deoxycytosine by three bases in the 3'→5' direction in the base side branch using 5'-dimethoxytrityl-N4-(O-levulinyl-6-oxyhexyl)-5-methyl-2'-deoxycytidine, 3'-[(2-cyanoethyl)-(N,N-diisopropyl)]-phosphoramidite (trade name: 5-Me-dC Brancher Phosphoramidite, Glen Research).

(T-$NH_2$) represents that synthesized using 5'-dimethoxytrityl-5-[N-(trifluoroacetylaminohexyl)-3-acryl imido]-2'-deoxyuridine, 3'-[(2-cyanoethyl)-(N,N-diisopropyl)]-phosphoramidite (trade name: Amino-Modifier C6 dT, Glen Research).

(B) represents that synthesized using [1-N-(4,4'-dimethoxytrityl)-biotinyl-6-aminohexyl]-2-cyanoethyl-(N,N-diisopropyl)-phosphoramidite (trade name: 5'-Biotin Phosphoramidite, Glen Research).

(spc18) represents that synthesized using 18-O-dimethoxytritylhexaethylene glycol, 1-[(2-cyanoethyl)-(N,N-diisopropyl)]-phosphoramidite (trade name: Spacer Phosphoramidite 18, Glen Research).

(Puromycin) represents that synthesized using 5'-dimethoxytrityl-N-trifluoroacetyl-puromycin, 2'-succinoyl-long chain alkylamino-CPG (trade name: Puromycin-CPG, Glen Research).

1-2 Synthesis and Purification Methods (1) Reduction of Puromycin Segment

18 µl of 2.5 mM puromycin segment and 90 µl of 1 M phosphate buffer (pH 9.0) were mixed followed by the addition of 10 µl of 1 M DTT and reacting for 1 hour at room temperature to reduce the disulfide group on the 5'-side of the puromycin segment to a thiol group. Subsequently, excess DTT was removed using an NAP-5 column (GE Healthcare Japan) equilibrated with 20 mM phosphate buffer (pH 7.2).

(2) EMCS Modification of PC-Branch-Thiol Segment

10 µl of 1 mM PC-Branch-Thiol segment were mixed with 100 µl of 0.2 M phosphate buffer (pH 7.2) followed by the addition of 20 µl of 0.1 M divalent crosslinking agent EMCS (6-maleimidohexanoic acid N-hydroxysuccinimide ester, Dojindo Laboratories), stirring well and reacting for 30 minutes at 37° C. Subsequently, the reaction product was precipitated by ethanol precipitation followed by removal of unreacted EMCS. The precipitate was washed with 200 µl of 70% ethanol.

(3) Crosslinking of Puromycin Segment and PC-Branch-Thiol Segment or PC-Branch-Biotin Segment The precipitate of the aforementioned EMCS-crosslinked PC-Branch-Thiol segment or the precipitate of the aforementioned EMCS-crosslinked PC-Branch-Biotin segment was dissolved in a solution of the aforementioned reduced puromycin segment (approx. 20 nmol) and allowed to stand overnight at 4° C.

Subsequently, the reaction product was precipitated by ethanol precipitation. After washing the precipitate with 200 µl of 70% ethanol, the precipitate was dissolved in 30 µl of sterile water. The resulting crosslinked product was separated by 8 M urea/12% polyacrylamide gel electrophoresis followed by staining with SybrGold (Invitrogen).

Figure 6:
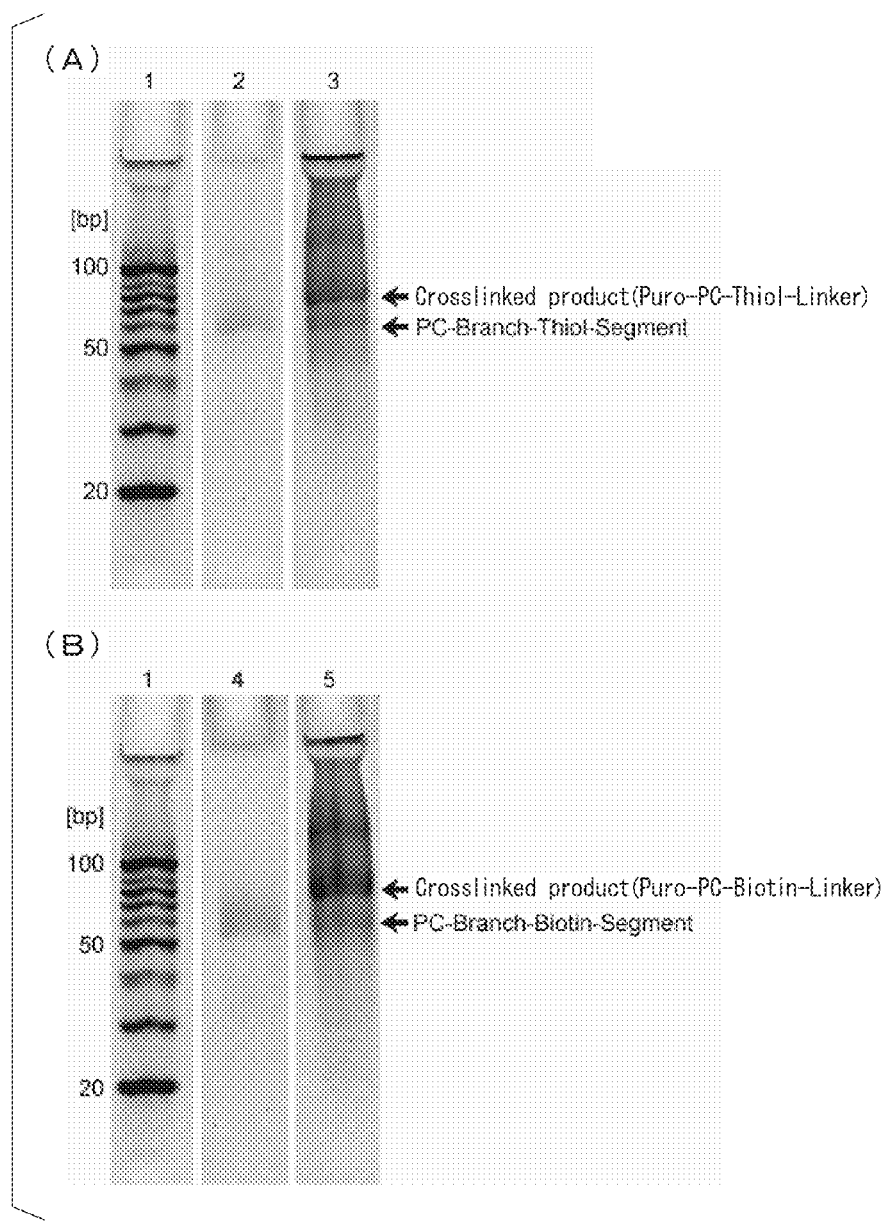
FIG. 6 indicates the results of electrophoresis in an example.

The results are shown in FIG. 6. Lane 1 is a 10 bp DNA step ladder (Promega), lane 2 is the PC-Branch-Thiol segment, Lane 3 is the crosslinked product of the PC-Branch-Thiol segment and the puromycin segment, lane 4 is the PC-Branch-Biotin segment, and lane 5 is the crosslinked product of the PC-Branch-Biotin segment and puromycin segment. The target crosslinked products (Puro-PC-Thiol linker and Puro-PC-Biotin linker) were confirmed to be obtained from lanes 3 and 5.

(4) HPLC Purification of Puro-PC-Thiol Linker and Puro-PC-Biotin Linker

The Puro-PC-Thiol linker and Puro-PC-Biotin linker synthesized in the manner described above were purified by HPLC.

(Synthesis of mRNA)

The B-domain of Protein A (to be referred to as BDA, SEQ ID NO: 2, 367 bp), obtained by adding a T7 promoter sequence and translation promoting sequence upstream from the 5'-side and adding a spacer region and sequence having a complementary strand region with the Puro-PC-Thiol linker or Puro-PC-Biotin linker downstream from the 3'-side, was amplified by PCR.

5 pmol/µl to 30 pmol/µl mRNA (337 b) was synthesized from the DNA obtained by PCR using the T7 RiboMAX Express Large Scale RNA Production System (Promega) in accordance with the protocol provided.

5 pmol of the aforementioned mRNA and 10 pmol of the Puro-PC-Thiol linker or 10 pmol of the Puro-PC-Biotin linker were mixed in T4 RNA Ligase buffer (Takara Bio) and heated to 90° C. followed by cooling to 25° C. over the course of 15 minutes. 0.5 µl of T4 polynucleotide kinase (10 U/µl, Toyobo) and 0.5 µl of T4 RNA ligase (40 U/µl, Takara Bio) were added to this solution and mixed therein followed by reacting for 15 minutes at 25° C.

Figure 7:
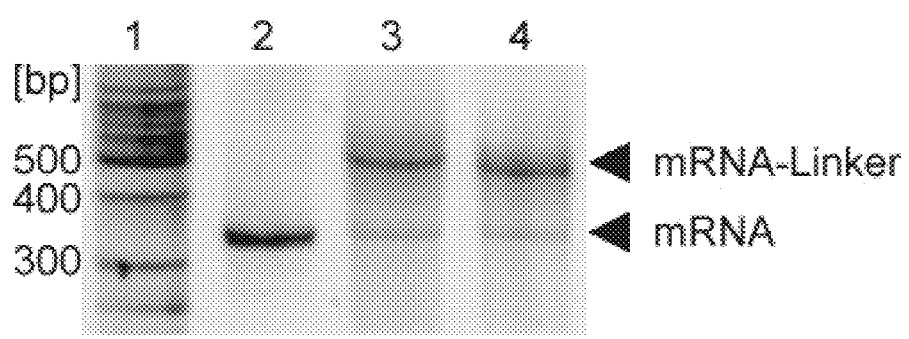
FIG. 7 indicates the results of electrophoresis in an example.

The reaction product was separated by 8 M urea/8% polyacrylamide gel electrophoresis and stained with SybrGold (Invitrogen). The results are shown in FIG. 7.

Lane 1 is a 100 bp DNA ladder (Promega), lane 2 is mRNA (BDA), lane 3 is the ligation product of the Puro-PC-Thiol linker and mRNA (BDA), and lane 4 is the ligation product of the Puro-PC-Biotin linker and mRNA (BDA).

Both the Puro-PC-Thiol linker and Puro-PC-Biotin linker linked with the mRNA and the bands were able to be observed to shift towards the high molecular weight side, thereby confirming that the synthesized nucleic acid linkers have the ability to link with mRNA.

Figure 8:
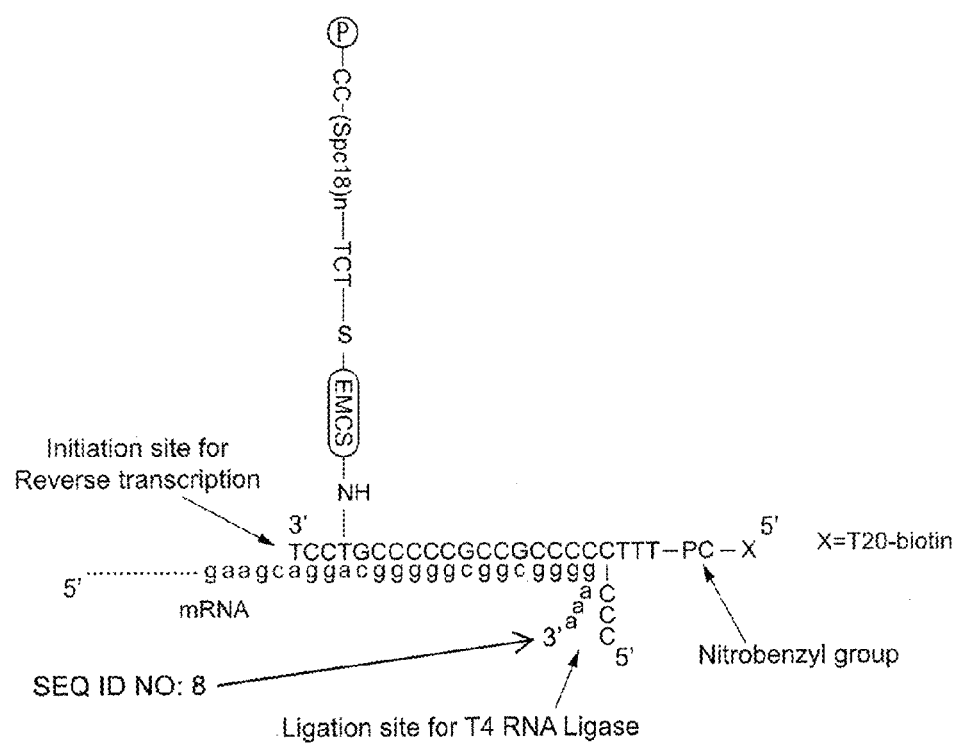
FIG. 8 is a schematic drawing of the hybridization product of BDA (B-domain of Protein A) mRNA and a nucleic acid linker in an example.

FIG. 8 shows a schematic diagram of the hybridization product of BDA and a nucleic acid linker. In FIG. 8, P indicates puromycin and PC indicates a photocleavage site (nitrobenzyl group). Upper case letters indicate the DNA segment while lower case letters indicate the mRNA segment. X indicates 5'-(B)-TTTTTTTTTTTTTTTTTTTT (SEQ ID NO: 10)-3'.

(Translation by Cell-Free Translation System)

Translation reactions were carried out using the nucleic acid linker and mRNA ligation products synthesized in the manner described above. RNase-free water was added and mixed with 1 pmol of mRNA-nucleic acid linker ligation product (mRNA-Linker ligation product), 0.72 µl of 20× Translation Mix (Ambion), 10.2 µl of rabbit reticulocyte cell lysate in the form of Rabbit Retic Lysate (Ambion) and 0.3 µl of Fluorotect (Promega) to obtain 15 µl of a mixture.

After allowing this mixture to react for 20 minutes at 30° C., 6 µl of 3 M calcium chloride solution and 1.8 µl of 1 M magnesium chloride solution were added and mixed therein. This mixture was then allowed to react for 30 minutes at 37° C. to synthesize a polypeptide chain of BDA gene and form an mRNA-nucleic acid linker-protein complex. The reaction product was separated by SDS containing 8 M urea/6% polyacrylamide gel electrophoresis, and the fluorescence signal of Fluorotect that had been incorporated in the protein was detected.

Figure 9:
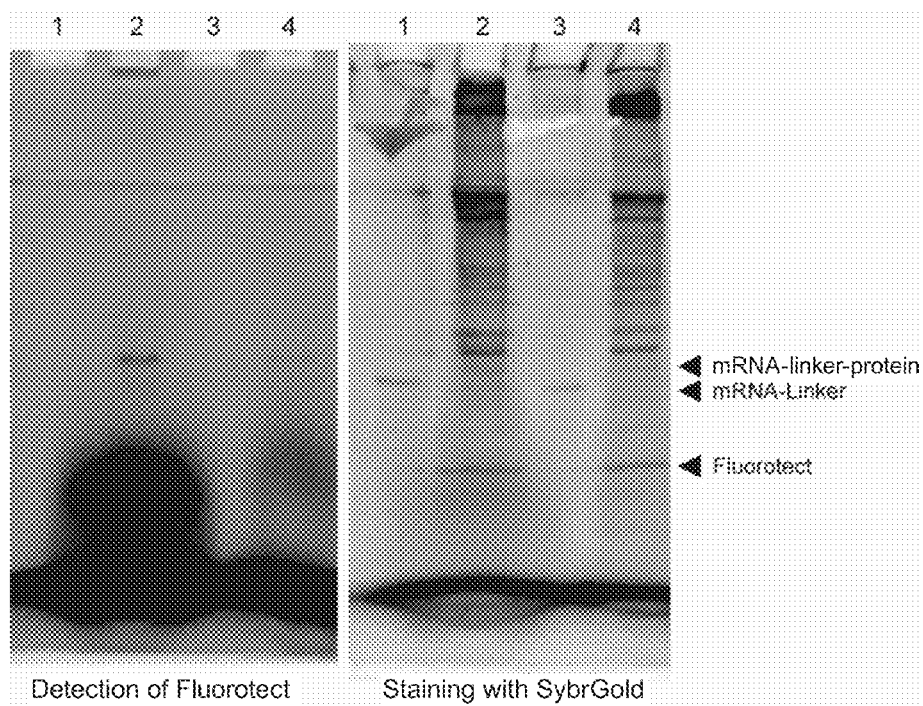
FIG. 9 indicates the results of electrophoresis in an example.

Moreover, mRNA was detected by staining the reaction product with SybrGold (Invitrogen). The results are shown in FIG. 9.

Lane 1 is the ligation product of the Puro-PC-Thiol linker and mRNA (BDA), lane 2 is the translation product of the ligation product of the Puro-PC-Thiol linker and mRNA (BDA), lane 3 is the ligation product of the Puro-PC-Biotin linker and mRNA (BDA), and lane 4 is the translation product of the ligation product of the Puro-PC-Biotin linker and mRNA (BDA).

According to the results of electrophoresis, bands of the mRNA-protein complex were able to be confirmed that demonstrated a fluorescence signal farther to the high molecular weight side than mRNA, thereby confirming that the synthesized nucleic acid linkers have the ability to display protein.

(Wavelength Dependency of Photocleavage of Nitrobenzyl Group-Inserted DNA)

Synthesis of the nitrobenzyl group-inserted DNA indicated below was commissioned to JBioS, and synthesis was carried out using an automated nucleic acid synthesizer in accordance with the phosphoramidite method.

[Sequence: 5'-(B)-(PC)-X2-(F)-3']

X2 represents the sequence indicated below.

N46 (46 mer random sequence consisting of A:T:G:C=1:1:1:1)

(F) indicates Fluorescent-dI, while (B) and (PC) are the same as previously defined.

Figure 10:
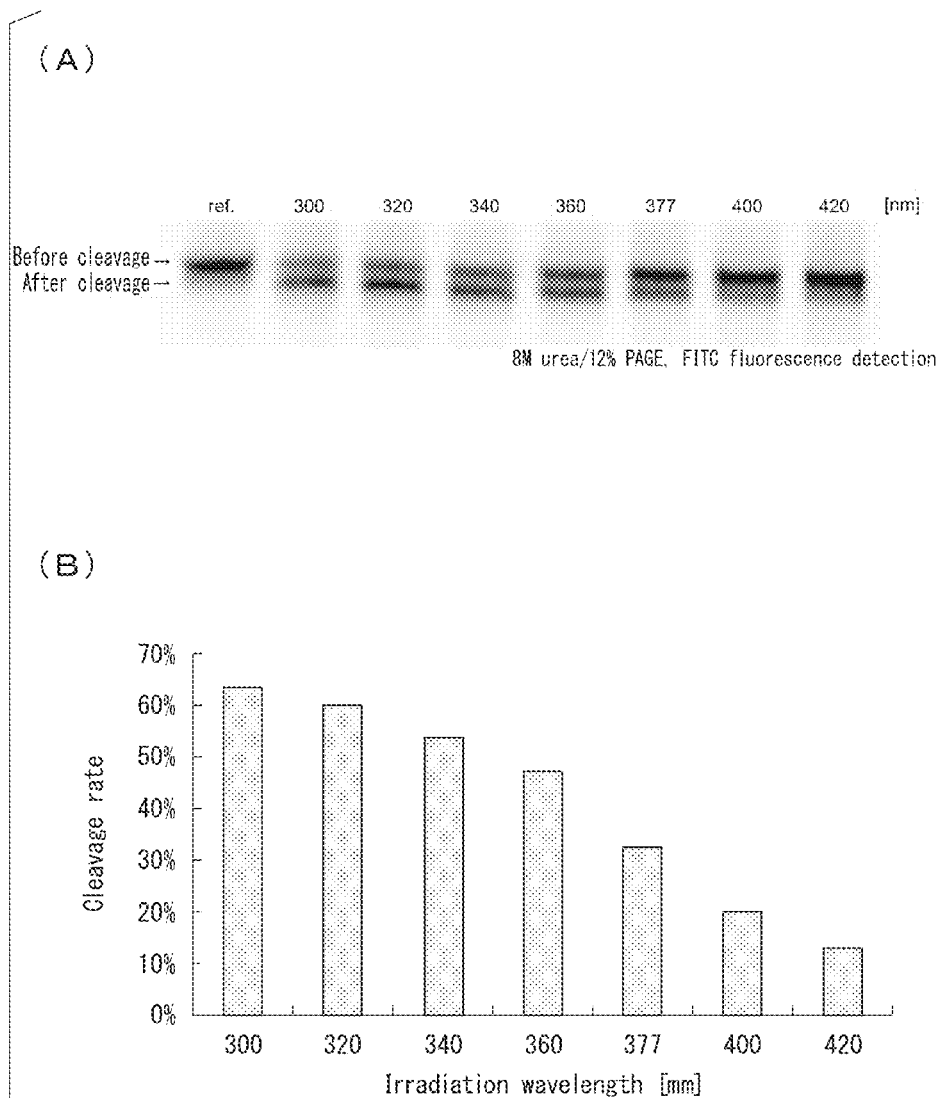
FIG. 10 indicates the results of examining the wavelength-dependency of photocleavage of DNA inserted with a nitrobenzyl group in an example.

400 µl an aqueous solution (10 µM) of the aforementioned nitrobenzyl group-inserted DNA was photoirradiated at 300 nm to 420 nm in a quartz cuvette using a fluorescence spectrophotometer followed by analyzing 10 µl (1 pmol) of the irradiated sample by PAGE. The results are shown in FIG. 10. The irradiation conditions were as indicated below.

Irradiation Conditions
Light source: 15 W Xe lamp
Light intensity: 0.15 mW/mm$^2$ to 0.31 mW/mm$^2$
Photoirradiated area: 50 mm$^2$ (5 mm×10 mm)
Irradiation time: 180 sec
Quartz cuvette dimensions: 2.5 mm×13 mm×10 mm (irradiation area: 2.5 mm×13 mm)
Temperature: Room temperature
Details of Light Intensity
300 nm: 0.15 mW/mm$^2$
320 nm: 0.20 mW/mm$^2$
340 nm: 0.25 mW/mm$^2$ 360 nm: 0.30 mW/mm$^2$
377 nm: 0.31 mW/mm$^2$
400 nm: 0.26 mW/mm$^2$
420 nm: 0.24 mW/mm$^2$ The upper portion of FIG. 10 (FIG. 10(A)) indicates the results of separating the photoirradiated nitrobenzyl group-inserted DNA by 12% polyacrylamide gel electrophoresis containing 8 M urea followed by detection of the resulting fluorescence signal. The lower portion of FIG. 10 (FIG. 10(B)) indicates the results of quantifying the results obtained in the upper portion of FIG. 10 (FIG. 10(A)). Cleavage rate refers to the value obtained by calculating according to (fluorescence signal intensity after cleavage)/[(fluorescence signal intensity before cleavage)+(fluorescence signal intensity after cleavage)].

Based on FIG. 10, although the nitrobenzyl group-inserted DNA was confirmed to be able to be cleaved by light having a wavelength in the vicinity of 300 nm, the nitrobenzyl group-inserted DNA was confirmed to be able to be cleaved by light having a wavelength of 350 nm to 400 nm that is associated with little damage to DNA.

(Preparation of Biotin-Modified, Nitrobenzyl Group-Inserted Double-Stranded DNA)

Biotin-modified, nitrobenzyl group-inserted double-stranded DNA was prepared using the oligonucleotide sets indicated below (DR(2His)PC-BTB or DRBio(2His) and Anti-Dr(GFPuv5)TexasRed).

The sequences of the oligonucleotides used were as indicated below.

(1) DR(2His)PC-BTB

[Sequence: 5'-(B)-T-(B)-TTTTTTTT-(PC)-X3-3']

X3 represents the sequence indicated below.

(SEQ ID NO: 3, 27 mer)
TATTCATTATTAGTGGTGGTGGTGGTG (B) and (PC) are the same as previously defined.
(2) DRBio(2His)
[Sequence: 5'-(B)-X3-3']
X3 is the same as indicated above.
(3) Anti-Dr(GFPuv5)TexasRed
[Sequence: 5'-TexasRed-X5-3']
X4 represents the sequence indicated below.

(SEQ ID NO: 4, 27 mer)
CACCACCACCACCACTAATAATGAATA

Reaction solutions having the compositions shown in Table 1 were prepared and allowed to stand undisturbed for 30 minutes at room temperature.

TABLE 1

| | |
|---|---|
| DR(2His)PC-BTB (10 µM) or DRBio(2His) (10 µM) | 1 µl |
| Anti-Dr(GFPuv5)TexasRed (10 µM) | 2 µl |
| 2× binding buffer | 2 µl |
| Nuclease-free water | 15 µl |
| Total | 20 µl |

(Pretreatment of Streptavidin-Modified Magnetic Beads)
35 µl of streptavidin-modified magnetic beads (SPHERO Streptavidin-Coated Magnetic Particle SVM-80-5, φ0.8 µm, 1.0% w/v) were washed three times with 35 µl of 1× binding buffer followed by suspending in 35 µl of 1× binding buffer.

(Immobilization of Biotin-Modified, Nitrobenzyl Group-Inserted Double-Stranded DNA)

Figure 11:
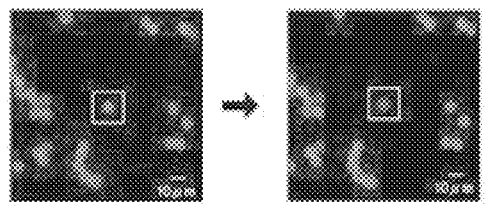
FIG. 11 indicates the results of measuring photocleaved DNA with a confocal laser scanning microscope in an example.
Figure 11:
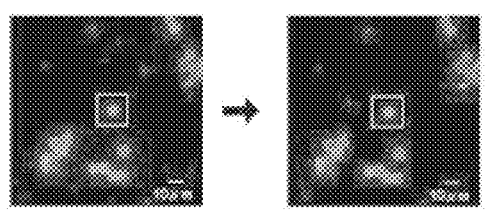
Figure 11:
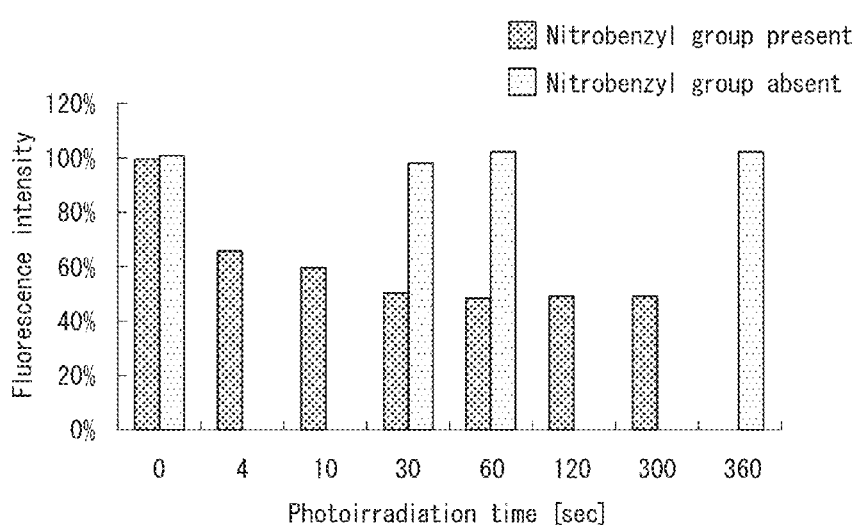

The supernatant was removed from 10 µl of the suspension of pretreated streptavidin-modified magnetic beads, and the suspension were suspended in solutions having the compositions shown in Table 1 after reacting followed by stirring for 30 minutes at room temperature. Next, after washing the beads in the suspension three times with 20 µl of 1× binding buffer, the beads were suspended in 100 µl of 1× binding buffer. A cover glass containing a drop of the suspension was photoirradiated using a confocal laser scanning microscope (Nikon C1) followed by observation thereof. The results are shown in FIG. 11. Furthermore, the conditions for photoirradiation and observation were as indicated below.

Photoirradiation Conditions
Object lens: 20×S Fluor (NA: 0.75)
Light source: 377 nm laser
Light intensity: 18 µW
Irradiated area: 19.7×19.7 µm$^2$
Scanning density: 1024×1024 pixels As shown in the upper portion of FIG. 11 (FIG. 11(A)), fluorescence intensity was confirmed to decrease as a result of photoirradiation in the magnetic beads on which were immobilized biotin-modified, double-stranded DNA inserted with a nitrobenzyl group. On the other hand, there were no changes in fluorescence intensity caused by photoirradiation in the magnetic beads on which were immobilized biotin-modified, double-stranded DNA not inserted with a nitrobenzyl group. The results of quantifying the results of FIG. 11(A) are shown in FIG. 11(B).

In this manner, in magnetic beads on which were immobilized biotin-modified, double-stranded DNA inserted with a nitrobenzyl group, the DNA was confirmed to be cleaved by photoirradiation and dissociated in the solvent.

(Preparation of Aminosilane-Modified Glass Substrate)

An 18 mm×18 mm cover glass (Matsunami Glass) was immersed in a solution consisting of 1:1 mixture (volume ratio) of concentrated sulfuric acid and aqueous hydrogen peroxide, and after allowing react for 15 minutes at 200° C., was cleaned with ultrapure water and dried by blowing with nitrogen gas (to be referred to as SPM cleaning).

Next, the aforementioned cover glass was immersed for 1 minute in 0.1 M NaOH solution followed by blowing with nitrogen gas to remove the solution from the cover glass.

Next, the aforementioned cover glass was immersed in a 0.1% aqueous acetic acid solution containing 1% APTES (3-aminopropyltriethoxysilane, Tokyo Chemical Industry), heated for 60 minutes at 90° C., and after cleaning for 1 minute with ethanol, was cleaned for 1 minute with ultrapure water followed by drying the glass by blowing with nitrogen gas to obtain an aminosilane-modified glass substrate.

(Production of Gold Thin Film-Deposited Glass Substrate)

Glass measuring 20 mm×20 mm and having a thickness of 0.5 mm was subjected to SPM cleaning followed by sputtering the aforementioned glass in the sequence of Cr for 30 seconds at 250 W followed by Au for 3 minutes at 100 W to produce a glass substrate deposited with a gold thin film having a thickness of 200 nm.

(Immobilization of Photocleavable DNA Oligomer on Gold Substrate)

The photocleavable DNA oligomer indicated below (DR(2His)-PC-T$_{30}$-SH) was synthesized based on an ordinary phosphoramidite method using an automated nucleic acid synthesizer. Furthermore, synthesis was commissioned to JBioS, and the finished product was delivered in a state in which the thiol group on the 5'-terminal was reduced with DTT. In addition, a DNA oligomer not having a photocleavage site (S-(T$_{20}$)Lin) was synthesized for use as a negative control.

(1) DR(2His)-PC-T$_{30}$-SH
[Sequence: 5'-(Thiol)-(T$_{30}$)-(PC)-X5-3']
X5 represents the sequence indicated below.

(SEQ ID NO: 5, 18 mer)
CCCGCCGCCCCCGTCCT

Here, (Thiol) represents a thiol group, and the oligomer was synthesized using Thiol-Modifier C6 S-S (Glen Research) for the reagent. (T30) represents a series of 30 deoxythymidine bases. (PC) is the same as previously defined.

(2) S-(T$_{20}$)Lin
[Sequence: 5'-(Thiol)-T$_{20}$-X6-3']
X6 represents the sequence indicated below.

(SEQ ID NO: 6, 17 mer)
CCCGCCGCCCCCGTCC (T$_{20}$) represents a series of 20 deoxythymidine bases. (Thiol) is the same as previously defined.

A gold substrate prepared in the manner previously described was subjected to SPM cleaning followed by immersing in 500 μL of photocleavable DNA oligomer adjusted to a concentration of 1 μM with 1×PBS and reacting for 4 hours at room temperature on the surface of the gold substrate to immobilize the photocleavable DNA oligomer on the gold substrate in the form of a thin film by gold-thiol bonding.

Next, the gold substrate was allowed to react for 1 hour in a 1 mM aqueous solution of 6-mercapto-1-hexanol followed by washing 5 times with 1×PBS and spin-drying.

(Preparation of Cy5 Fluorescent Dye-Introduced RNA)

GFP (SEQ ID NO: 7, 869 bp), having a T7 promoter sequence and translation promoting sequence upstream from the 5'-side and a spacer region and a sequence complementary to the DNA moiety of the aforementioned photocleavable DNA oligomer linker downstream from the 3'-side, and from which the termination codons had been excised, was amplified by PCR.

5 pmol/μl to 30 pmol/μl Cy5-introduced mRNA (839 b) was synthesized from the DNA obtained by PCR using the T7 RiboMAX Express Large Scale RNA Production System (Promega) and Cy5-UTP (GE Healthcare) in accordance with the protocols provided.

(Immobilization of Thiol-Modified, Nitrobenzyl Group-Inserted DNA/RNA)

The aforementioned Cy5-introduced mRNA was dissolved in 3×PBS containing 0.1% SDS to prepare a 0.6 pmol/μL mRNA solution. 10 μL of the mRNA solution were dropped onto a gold substrate under conditions of a temperature of 4° C. and a cover glass was placed thereon. Furthermore, the space between the gold substrate and cover glass was sealed with silicon grease.

After heating the gold substrate to 70° C. using a thermal cycler, the gold substrate was gradually cooled to 10° C. over the course of 15 minutes to hybridize the photocleavable oligomer DR (2His)-PC-T$_{30}$-SH with the Cy5-introduced mRNA. The gold substrate was then washed twice with 3×PBS containing 0.2% Tween 20, twice with 3×PBS and twice with 0.1×PBS.

(Photocleavage of DNA/mRNA Immobilized on Gold Substrate and Transcription and Adsorption to Amino Group-Modified Glass Cover)

7 μL of 0.1×PBS were dropped onto a gold substrate, and the aforementioned amino group-modified cover glass was placed thereon with the amino group-modified side facing towards the gold substrate. Furthermore, the space between the gold substrate and the amino group-modified cover glass was sealed using silicon grease.

Next, Cy5 fluorescent images were observed using a confocal laser scanning microscope (Ex: 633 nm, Em: 655-710 nm BP) to confirm that the Cy5-introduced mRNA had been hybridized.

Figure 12:
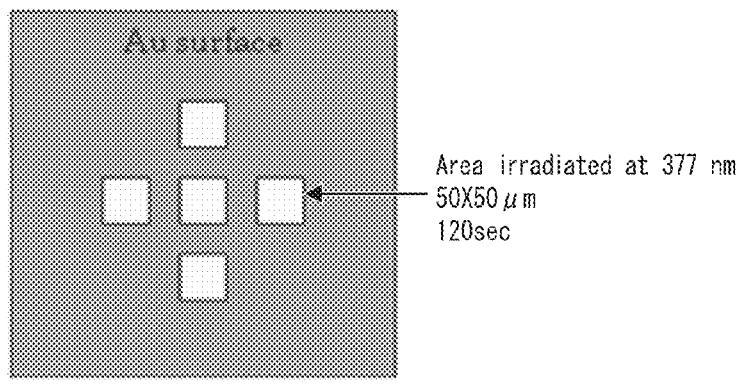
FIG. 12 depicts fluorescent images of a DNA/mRNA complex on a gold substrate and amino group-modified glass cover following photoirradiation in an example.
Figure 12:
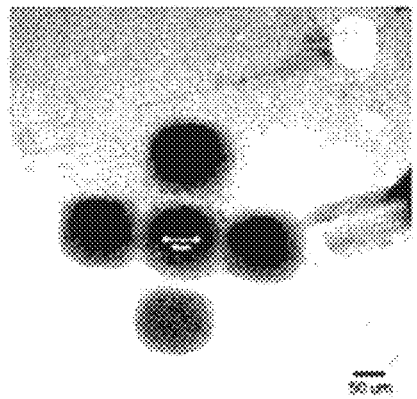
Figure 12:
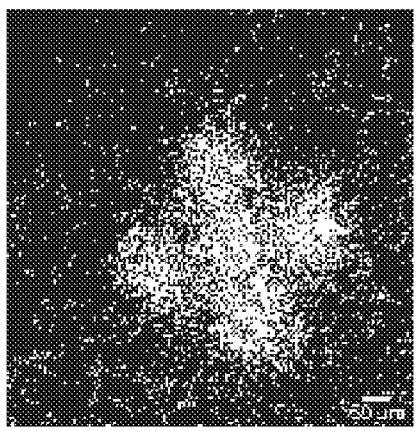

Next, a region measuring 50 μm×50 μm on the gold substrate was irradiated with laser light (8.3 μW) for 120 seconds using a confocal laser scanning microscope as shown in FIG. 12(A) to cleave the photocleavable group of the immobilized DNA. After irradiating with 377 nm laser light, the gold substrate was allowed to stand for 30 minutes at room temperature followed by removing the amino group-modified cover glass, and observing the DNA cleavage pattern on the gold substrate as well as the DNA adsorption pattern on the amino group-modified cover glass with a confocal laser scanning microscope using fluorescence of the Cy5 used to modify the mRNA as an indicator. The DNA cleavage pattern on the gold substrate is shown in FIG. 12(B), while the DNA adsorption pattern on the amino group-modified cover glass is shown in FIG. 12(C).

In FIG. 12(B), since fluorescence was not detected at the locations corresponding to the areas irradiated with laser light indicated in FIG. 12(A), the photocleavage site of the DNA was confirmed to have been cleaved by laser irradiation.

On the other hand, in FIG. 12(C), since fluorescence was detected at the locations corresponding to the areas irradiated with laser light indicated in FIG. 12(A), the photocleaved DNA was confirmed to have been adsorbed to the amino group-modified cover glass.

In this manner, region-specific photocleavage and recovery on a gold thin film were confirmed to be possible.

On the basis of the above results, it is clear from the present embodiment that nucleic acid can be efficiently recovered from a specific region on a solid phase.

INDUSTRIAL APPLICABILITY

An object of embodiments of the present invention is to provide a protein-immobilizing solid phase and a polynucleotide-immobilizing solid phase that enable nucleic acid to be efficiently recovered from a solid phase, and a method for efficiently recovering nucleic acid.

According to embodiments of the present invention, nucleic acid can be efficiently recovered from a solid phase.

What is claimed is:

1. A protein-immobilizing solid phase comprising an mRNA-nucleic acid linker-protein complex, obtained by linking the mRNA and the protein encoded by that mRNA through the nucleic acid linker, immobilized on the solid phase; wherein, the nucleic acid linker comprises a linker selected from the group consisting of linker (a) and linker (b), the linker (a) comprises a first 3'-terminal region, and a first and a second branched 5'-terminal regions, wherein the first 3'-terminal region comprises (i) a single-stranded polynucleotide segment that hybridizes with the nucleic sequence on the 3'-terminus of the mRNA, and (ii) an arm segment branched from the single-stranded polynucleotide segment, and having a linking segment with the protein on a terminus of the linking segment, the first branched 5'-terminal region comprises a bonding site with the first 3'-terminal of the mRNA, and the second branched 5'-terminal region comprises a photocleavage site and a solid phase binding site on the 5'-terminal; and the linker (b) comprises a second 3'-terminal region, and a third 5'-terminal region, wherein the second 3'-terminal region comprises (i) a single-stranded polynucleotide segment that hybridizes with the nucleic sequence on the 3'-terminus of the mRNA, and (ii) an arm segment that comprises a first photocleavage site on the 5'-terminus of the arm segment, is branched from the single-stranded polynucleotide segment, and comprises a linking segment with the aforementioned protein on a terminus of the linking segment, and the third 5'-terminal region comprises, in order starting from the 5'-terminus, a bonding site with the 3'-terminal of the mRNA, a second photocleavage site, and a solid phase binding site branched from between the first photocleavage site and the second cleavage site.

2. The protein-immobilizing solid phase according to claim 1, wherein the nucleic acid linker comprises the linker (a).

3. The protein-immobilizing solid phase according to claim 1, wherein the nucleic acid linker comprises the linker (b).

4. The protein-immobilizing solid phase according to claim 1, wherein the linking segment comprises a segment selected from the group consisting of a puromycin, a 3'-N-aminoacyl puromycin aminonucleoside, and a 3'-N-aminoacyl adenosine aminonucleoside bound to an end of the arm segment.

5. The protein-immobilizing solid phase according to claim 1, wherein the nucleic acid linker has (a) only one 3'-terminal region, which is the first 3'-terminal region, and only two 5'-terminal regions, which are the first and second branched 5'-terminal regions, or (b) only one 3'-terminal region, which is the second 3'-terminal region, and only one 5'-terminal region, which is the third 5' terminal region.

6. A protein-immobilizing solid phase comprising an mRNA/cDNA-nucleic acid linker-protein complex, obtained by linking the mRNA/cDNA, composed of the mRNA and the cDNA complementary to the mRNA, and the protein encoded by that mRNA through the nucleic acid linker, immobilized on the solid phase; wherein, the nucleic acid linker comprises a linker selected from the group consisting of linker (a) and linker (b), the linker (a) comprises a first 3'-terminal region, and a first and a second branched 5'-terminal regions, wherein the first 3'-terminal region comprises (i) a single-stranded polynucleotide segment that hybridizes with the nucleic sequence on the 3'-terminus of the mRNA, and (ii) an arm segment branched from the single-stranded polynucleotide segment and having a linking segment with the protein on a terminus of the linking segment, the first branched 5'-terminal region comprises a bonding site with the first 3'-terminal of the mRNA, and the second branched 5'-terminal region comprises a photocleavage site and a solid phase binding site on the 5'-terminal; and the linker (b) comprises a second 3'-terminal region, and a third 5'-terminal region, wherein the second 3'-terminal region comprises (i) a single-stranded polynucleotide segment that hybridizes with the nucleic sequence on the 3'-terminus of the mRNA, and (ii) an arm segment that comprises a first photocleavage site on the 5'-terminus of the arm segment, is branched from the single-stranded polynucleotide segment, and comprises a linking segment with the aforementioned protein on a terminus of the linking segment, and the third 5'-terminal region comprises, in order starting from the 5'-terminus, a bonding site with the 3'-terminal of the mRNA, a second photocleavage site, and a solid phase binding site branched from between the first photocleavage site and the second cleavage site.

7. The protein-immobilizing solid phase according to claim 6, wherein the nucleic acid linker comprises the linker (a).

8. The protein-immobilizing solid phase according to claim 6, wherein the nucleic acid linker comprises the linker (b).

9. The protein-immobilizing solid phase according to claim 6, wherein the nucleic acid linker has (a) only one 3'-terminal region, which is the first 3'-terminal region, and only two 5'-terminal regions, which are the first and second branched 5'-terminal regions, or (b) only one 3'-terminal region, which is the second 3'-terminal region, and only one 5'-terminal region, which is the third 5' terminal region.

10. A polynucleotide-immobilizing solid phase comprising a polynucleotide-nucleic acid linker complex, obtained by linking the polynucleotide and the nucleic acid linker, immobilized on the solid phase, wherein the nucleic acid linker comprises a linker selected from the group consisting of linker (a) and linker (b), the linker (a) comprises a first 3'-terminal region, and a first and a second branched 5'-terminal regions, wherein the first 3'-terminal region comprises a single-stranded polynucleotide segment that hybridizes with the nucleic sequence on the 3'-terminus of the polynucleotide, the first branched 5'-terminal region comprises a bonding site with the first 3'-terminal of the polynucleotide, and the second branched 5'-terminal region comprises a photocleavage site and a solid phase binding site on the 5'-terminal; and the linker (b) comprises a second 3'-terminal region, and a third 5'-terminal region, wherein the second 3'-terminal region comprises (i) a single-stranded polynucleotide segment that hybridizes with the nucleic sequence on the 3'-terminus of the polynucleotide, and a first photocleavage site on the 5'-terminus of the second 3'-terminal region, and the third 5'-terminal region comprises, in order starting from the 5'-terminus, a bonding site with the 3'-terminal of the polynucleotide, a second photocleavage site, and a solid phase binding site branched from between the first photocleavage site and the second cleavage site.

11. The polynucleotide-immobilizing solid phase according to claim 10, wherein the nucleic acid linker comprises the linker (a).

12. The polynucleotide-immobilizing solid phase according to claim 10, wherein the nucleic acid linker comprises the linker (b).

13. The protein-immobilizing solid phase according to claim 10, wherein the nucleic acid linker has (a) only one 3'-terminal region, which is the first 3'-terminal region, and only two 5'-terminal regions, which are the first and second branched 5'-terminal regions, or (b) only one 3'-terminal region, which is the second 3'-terminal region, and only one 5'-terminal region, which is the third 5' terminal region.

14. A protein-immobilizing solid phase comprising an mRNA-nucleic acid linker-protein complex, obtained by linking the mRNA and the protein encoded by that mRNA through the nucleic acid linker, immobilized on the solid phase, wherein
the nucleic acid linker comprises a linker selected from the group consisting of linker (a) and linker (b),
the linker (a) comprises a first 3'-terminal region, and a first and a second branched 5'-terminal regions, wherein
the first 3'-terminal region comprises (i) a single-stranded polynucleotide segment that hybridizes with the nucleic sequence on the 3'-terminus of the mRNA, and (ii) an arm segment branched from the single-stranded polynucleotide segment and having a linking segment with the protein on a terminus of the linking segment,
the first branched 5'-terminal region comprises a bonding site with the first 3'-terminal of the mRNA, and
the second branched 5'-terminal region comprises a cleavage site and a solid phase binding site on the 5'-terminal; or
the linker (b) comprises a second 3'-terminal region, and a third 5'-terminal region, wherein
the second 3'-terminal region comprises (i) a single-stranded polynucleotide segment that hybridizes with the nucleic sequence on the 3'-terminus of the mRNA, and (ii) an arm segment that comprises a first cleavage site on the 5'-terminus of the arm segment, is branched from the single-stranded polynucleotide segment, and comprises a linking segment with the aforementioned protein on a terminus of the linking segment, and
the third 5'-terminal region comprises, in order starting from the 5'-terminus, a bonding site with the 3'-terminal of the mRNA, a second cleavage site, and a solid phase binding site branched from between the first cleavage site and the second cleavage site.

15. The protein-immobilizing solid phase according to claim 14, wherein the protein comprises any one of an enzyme, antibody, antigen, aptamer and peptide.

16. The protein-immobilizing solid phase according to claim 14, wherein the nucleic acid linker comprises the linker (a).

17. The protein-immobilizing solid phase according to claim 14, wherein the nucleic acid linker comprises the linker (b).

18. The protein-immobilizing solid phase according to claim 14, wherein the nucleic acid linker has (a) only one 3'-terminal region, which is the first 3'-terminal region, and only two 5'-terminal regions, which are the first and second branched 5'-terminal regions, or (b) only one 3'-terminal region, which is the second 3'-terminal region, and only one 5'-terminal region, which is the third 5' terminal region.

19. A polynucleotide-immobilizing solid phase comprising a polynucleotide-nucleic acid linker complex, obtained by linking the polynucleotide and the nucleic acid linker, immobilized on the solid phase, wherein
the nucleic acid linker comprises one 3'-terminal region, and a first and a second branched 5'-terminal regions,
the 3'-terminal region comprises a single-stranded polynucleotide segment that hybridizes with the nucleic sequence on the 3'-terminus of the polynucleotide,
the first branched 5'-terminal region comprises a bonding site with the 3'-terminal of the polynucleotide, and
the second branched 5'-terminal region comprises a cleavage site and a solid phase binding site on the 5'-terminal.

20. A nucleic acid recovery method having a step for recovering an mRNA-protein complex, an mRNA/cDNA-protein complex or a polynucleotide using the immobilizing solid phase according to claim 1 by cleaving the nucleic acid linker at a photocleavage site of the nucleic acid linker by photoirradiating the immobilizing solid phase.

21. A nucleic acid recovery method having a step for recovering an mRNA-protein complex, an mRNA/cDNA-protein complex or a polynucleotide using the immobilizing solid phase according to claim 19 by cleaving the nucleic acid linker at a cleavage site of the nucleic acid linker.

* * * * *

SEQUENCE LISTING

<160> NUMBER OF SEQ ID NOS: 10

<210> SEQ ID NO 1
<211> LENGTH: 15

```
<212> TYPE: DNA
<213> ORGANISM: Artificial Sequence
<220> FEATURE:
<223> OTHER INFORMATION: B-domain of Protein A mRNA

<400> SEQUENCE: 1
ccccgccgcc ccccg                                                    15

<210> SEQ ID NO 2
<211> LENGTH: 367
<212> TYPE: DNA
<213> ORGANISM: Artificial Sequence
<220> FEATURE:
<223> OTHER INFORMATION: Synthetic: Protein A B-domain

<400> SEQUENCE: 2
gatcccgcga aattaatacg actcactata ggggaagtat ttttacaaca attaccaaca    60
acaacaacaa acaacaacaa cattacattt tacattctac aactacaagc caccatggat   120
aacaaattca acaagaaca acaaaatgct ttctatgaaa tcttacattt acctaactta    180
aacgaagaac aacgcaatgg tttcatccaa agcctaaaag atgacccaag ccaaagcgct   240
aaccttttag cagaagctaa aaagctaaat gatgctcaag caccaaaagc tgacaacaaa   300
ttcaacgggg gaggcagcca tcatcatcat catcacggcg aagcaggac ggggggcggc   360 ggggaaa                                                            367

<210> SEQ ID NO 3
<211> LENGTH: 27
<212> TYPE: DNA
<213> ORGANISM: Artificial Sequence
<220> FEATURE:
<223> OTHER INFORMATION: Synthetic - X3

<400> SEQUENCE: 3
tattcattat tagtggtggt ggtggtg                                       27

<210> SEQ ID NO 4
<211> LENGTH: 27
<212> TYPE: DNA
<213> ORGANISM: Artificial Sequence
<220> FEATURE:
<223> OTHER INFORMATION: Synthetic - X4

<400> SEQUENCE: 4
caccaccacc accactaata atgaata                                       27

<210> SEQ ID NO 5
<211> LENGTH: 18
<212> TYPE: DNA
<213> ORGANISM: Artificial Sequence
<220> FEATURE:
<223> OTHER INFORMATION: Synthetic - X5

<400> SEQUENCE: 5
cccgccgccc cccgtcct                                                 18

<210> SEQ ID NO 6
<211> LENGTH: 17
<212> TYPE: DNA
<213> ORGANISM: Artificial Sequence
<220> FEATURE:
<223> OTHER INFORMATION: Synthetic - X6

<400> SEQUENCE: 6
```

```
cccgccgccc cccgtcc                                                      17
```

```
<210> SEQ ID NO 7
<211> LENGTH: 869
<212> TYPE: DNA
<213> ORGANISM: Artificial Sequence
<220> FEATURE:
<223> OTHER INFORMATION: Synthetic - GFP

<400> SEQUENCE: 7
gatcccgcga aattaatacg actcactata ggggaagtat ttttacaaca attaccaaca       60
acaacaacaa acaacaacaa cattacattt tacattctac aactacaagc caccatgagt      120
aaaggagaag aacttttcac tggagttgtc ccaattcttg ttgaattaga tggtgatgtt      180
aatgggcaca aattttctgt cagcggagag ggtgaaggtg atgcaacata cggaaaactt      240
acccttaaat ttatttgcac tactggaaaa ctacctgttc catggccaac acttgtcact      300
actctgacgt atggtgttca atgcttttcc cgttatccgg atcacatgaa acggcatgac      360
ttttttcaaga gtgccatgcc cgaaggttat gtacaggaac gcactatatc tttcaaagat      420
gacgggaact acaagacgcg tgctgaagtc aagtttgaag gtgataccct tgttaatcgt      480
atcgagttaa aaggtattga ttttaaagaa gatggaaaca ttctcggaca caaactcgag      540
tacaactata actcacacaa tgtatacatc acggcagaca acaaaagaa tggaatcaaa       600
gctaacttca aaactcgcca caacattgaa gatggctccg ttcaactagc agaccattat      660
cagcaaaata ctccaattgg cgatggccct gtccttttac cagacaacca ttacctgtcg      720
acacaatctg ccctttttgaa agatcccaac gaaaagcgtg accacatggt ccttcttgag      780
tttgtaactg ctgctgggat tacacatggc atggatgagc tctacaaaga attcgagctc      840
cgtcgacagg acgggggcg gcggggaaa                                          869
```

```
<210> SEQ ID NO 8
<211> LENGTH: 26
<212> TYPE: RNA
<213> ORGANISM: Artificial Sequence
<220> FEATURE:
<223> OTHER INFORMATION: B-domain of Protein A mRNA

<400> SEQUENCE: 8 aaagggcgg cggggcagg acgaag                                              26
```

```
<210> SEQ ID NO 9
<211> LENGTH: 30
<212> TYPE: DNA
<213> ORGANISM: Artificial Sequence
<220> FEATURE:
<223> OTHER INFORMATION: Part of PC-Branch-Thiol Segment

<400> SEQUENCE: 9
tttttttttt tttttttttt tttttttttt                                        30
```

```
<210> SEQ ID NO 10
<211> LENGTH: 20
<212> TYPE: DNA
<213> ORGANISM: Artificial Sequence
<220> FEATURE:
<223> OTHER INFORMATION: Part of PC-Branch-Biotin Segment

<400> SEQUENCE: 10
tttttttttt tttttttttt                                                   20
```